(12) United States Patent
Davenport et al.

(10) Patent No.: US 9,271,842 B2
(45) Date of Patent: Mar. 1, 2016

(54) EXPANDABLE TRIAL ASSEMBLY FOR EXPANDABLE VERTEBRAL IMPLANT

(75) Inventors: Daniel Davenport, Collegeville, PA (US); Colm McLaughlin, Philadelphia, PA (US); Derek Martzall, Sinking Springs, PA (US)

(73) Assignee: Globus Medical, Inc., Audubon, PA (US)

( * ) Notice: Subject to any disclaimer, the term of this patent is extended or adjusted under 35 U.S.C. 154(b) by 103 days.

(21) Appl. No.: 13/440,129

(22) Filed: Apr. 5, 2012

(65) Prior Publication Data

US 2012/0232660 A1    Sep. 13, 2012

Related U.S. Application Data

(63) Continuation-in-part of application No. 13/333,227, filed on Dec. 21, 2011, now Pat. No. 8,591,585, which is a continuation-in-part of application No. 12/758,529, filed on Apr. 12, 2010, now Pat. No. 8,282,683.

(51) Int. Cl.
*A61F 2/44* (2006.01)
*A61F 2/46* (2006.01)
(Continued)

(52) U.S. Cl.
CPC .............. *A61F 2/44* (2013.01); *A61F 2/4455* (2013.01); *A61F 2/4611* (2013.01); *A61F 2/4684* (2013.01); *A61F 2/4465* (2013.01); A61F 2002/2817 (2013.01); A61F 2002/2835 (2013.01); A61F 2002/3008 (2013.01); A61F 2002/3055 (2013.01); A61F 2002/30383 (2013.01); A61F 2002/30393 (2013.01); A61F 2002/30395 (2013.01); A61F 2002/30405 (2013.01); A61F 2002/30477 (2013.01); A61F 2002/30495 (2013.01); A61F 2002/30504 (2013.01); A61F 2002/30505 (2013.01); A61F 2002/30512 (2013.01); A61F 2002/30523 (2013.01); A61F 2002/30571 (2013.01); A61F 2002/30576 (2013.01); A61F 2002/30578 (2013.01); A61F 2002/30579 (2013.01); A61F 2002/30594 (2013.01);
(Continued)

(58) Field of Classification Search
CPC ................ A61F 2/4455–2/447; A61F 2/4611; A61F 2/4684; A61F 2/44; A61F 2002/30579; A61F 2002/30601; A61F 2/4657; A61F 2/4311; A61F 2002/4658–2002/4674
USPC .......... 606/86 A, 105, 102; 623/17.11–17.16; 600/587
See application file for complete search history.

(56) References Cited

U.S. PATENT DOCUMENTS 5,236,460 A * 8/1993 Barber ..................... 623/17.15
5,571,192 A * 11/1996 Schonhoffer .............. 623/17.11
(Continued)

*Primary Examiner* — Jacqueline Johanas

(57) ABSTRACT

The present invention relates to a method of inserting an implant comprising providing a trial assembly. The method may further comprise positioning the trial assembly between vertebrae in a patient. The method may further comprise rotating a drive shaft of the trial assembly to cause upper and lower gear members of the trial assembly to rotate causing expansion of a tip assembly of the trial assembly. The method may further comprise measuring expansion of the trial assembly with a scale at a proximal end of the trial assembly. The method may further comprise removing the trial assembly from the patient. The method may further comprise positioning an implant between the vertebrae in the patient. The method may further comprise expanding the implant based on the measured expansion of the trial assembly.

8 Claims, 18 Drawing Sheets

(51) Int. Cl.
  *A61F 2/28* (2006.01)
  *A61F 2/30* (2006.01)
(52) U.S. Cl.
  CPC ............... *A61F 2002/30598* (2013.01); *A61F 2002/30601* (2013.01); *A61F 2002/30604* (2013.01); *A61F 2002/30828* (2013.01); *A61F 2002/30843* (2013.01); *A61F 2002/30846* (2013.01); *A61F 2002/30858* (2013.01); *A61F 2002/4475* (2013.01); *A61F 2002/4625* (2013.01); *A61F 2002/4627* (2013.01); *A61F 2002/4628* (2013.01); *A61F 2002/4629* (2013.01); *A61F 2002/4658* (2013.01); *A61F 2002/4661* (2013.01); *A61F 2002/4668* (2013.01); *A61F 2310/00011* (2013.01); *A61F 2310/00023* (2013.01); *A61F 2310/00131* (2013.01)

(56) References Cited

U.S. PATENT DOCUMENTS

| | | | | |
|---|---|---|---|---|
| 5,702,455 | A * | 12/1997 | Saggar | 623/17.15 |
| 6,015,435 | A * | 1/2000 | Valunin et al. | 623/6.28 |
| 6,190,413 | B1 * | 2/2001 | Sutcliffe | 623/17.11 |
| 6,344,057 | B1 | 2/2002 | Rabbe | |
| 6,752,832 | B2 * | 6/2004 | Neumann | 623/17.15 |
| 7,976,549 | B2 * | 7/2011 | Dye et al. | 606/99 |
| 8,043,295 | B2 * | 10/2011 | Reed et al. | 606/90 |
| 8,114,092 | B2 * | 2/2012 | Altarac | A61F 2/4611 606/914 |
| 8,282,650 | B2 * | 10/2012 | Weber | A61F 2/4657 606/102 |
| 8,303,663 | B2 * | 11/2012 | Jimenez et al. | 623/17.16 |
| 8,512,348 | B2 * | 8/2013 | Chabansky et al. | 606/99 |
| 8,636,746 | B2 * | 1/2014 | Jimenez et al. | 606/99 |
| 8,771,360 | B2 * | 7/2014 | Jimenez et al. | 623/17.16 |
| 2002/0082695 | A1 * | 6/2002 | Neumann | 623/17.11 |
| 2005/0113842 | A1 * | 5/2005 | Bertagnoli | A61B 17/025 606/90 |
| 2006/0069436 | A1 * | 3/2006 | Sutton | A61F 2/4684 623/17.13 |
| 2006/0074431 | A1 * | 4/2006 | Sutton et al. | 606/90 |
| 2006/0084975 | A1 * | 4/2006 | Berry | 606/53 |
| 2006/0241770 | A1 | 10/2006 | Rhoda | |
| 2006/0264963 | A1 * | 11/2006 | Reed et al. | 606/90 |
| 2007/0028710 | A1 * | 2/2007 | Kraus et al. | 74/400 |
| 2007/0093850 | A1 * | 4/2007 | Harris | A61F 2/4611 606/99 |
| 2007/0191954 | A1 * | 8/2007 | Hansell et al. | 623/17.15 |
| 2007/0209222 | A1 * | 9/2007 | Fischer | A61F 2/4657 33/512 |
| 2007/0225726 | A1 * | 9/2007 | Dye et al. | 606/99 |
| 2007/0255408 | A1 * | 11/2007 | Castleman et al. | 623/17.11 |
| 2007/0255415 | A1 * | 11/2007 | Edie | A61F 2/44 623/17.16 |
| 2007/0260260 | A1 * | 11/2007 | Hahn | A61F 2/4657 606/102 |
| 2008/0109005 | A1 * | 5/2008 | Trudeau et al. | 606/99 |
| 2008/0140207 | A1 * | 6/2008 | Olmos et al. | 623/17.16 |
| 2009/0138089 | A1 | 5/2009 | Doubler | |
| 2009/0164017 | A1 | 6/2009 | Sommerich | |
| 2009/0182343 | A1 * | 7/2009 | Trudeau | A61F 2/4657 606/102 |
| 2009/0198245 | A1 * | 8/2009 | Phan | 606/99 |
| 2010/0114106 | A1 * | 5/2010 | Weber | A61F 2/4657 606/102 |
| 2010/0179655 | A1 | 7/2010 | Hansell | |
| 2010/0268234 | A1 * | 10/2010 | Aho et al. | 606/80 |
| 2010/0274357 | A1 | 10/2010 | Miller | |
| 2010/0286787 | A1 | 11/2010 | Villiers | |
| 2010/0298941 | A1 * | 11/2010 | Hes et al. | 623/17.16 |
| 2011/0106260 | A1 * | 5/2011 | Laurence | A61F 2/4425 623/17.16 |
| 2011/0218631 | A1 * | 9/2011 | Woodburn et al. | 623/17.16 |
| 2011/0251692 | A1 | 10/2011 | McLaughlin | |
| 2012/0029635 | A1 * | 2/2012 | Schoenhoeffer et al. | 623/17.11 |
| 2012/0191194 | A1 * | 7/2012 | Olmos et al. | 623/17.16 |

* cited by examiner

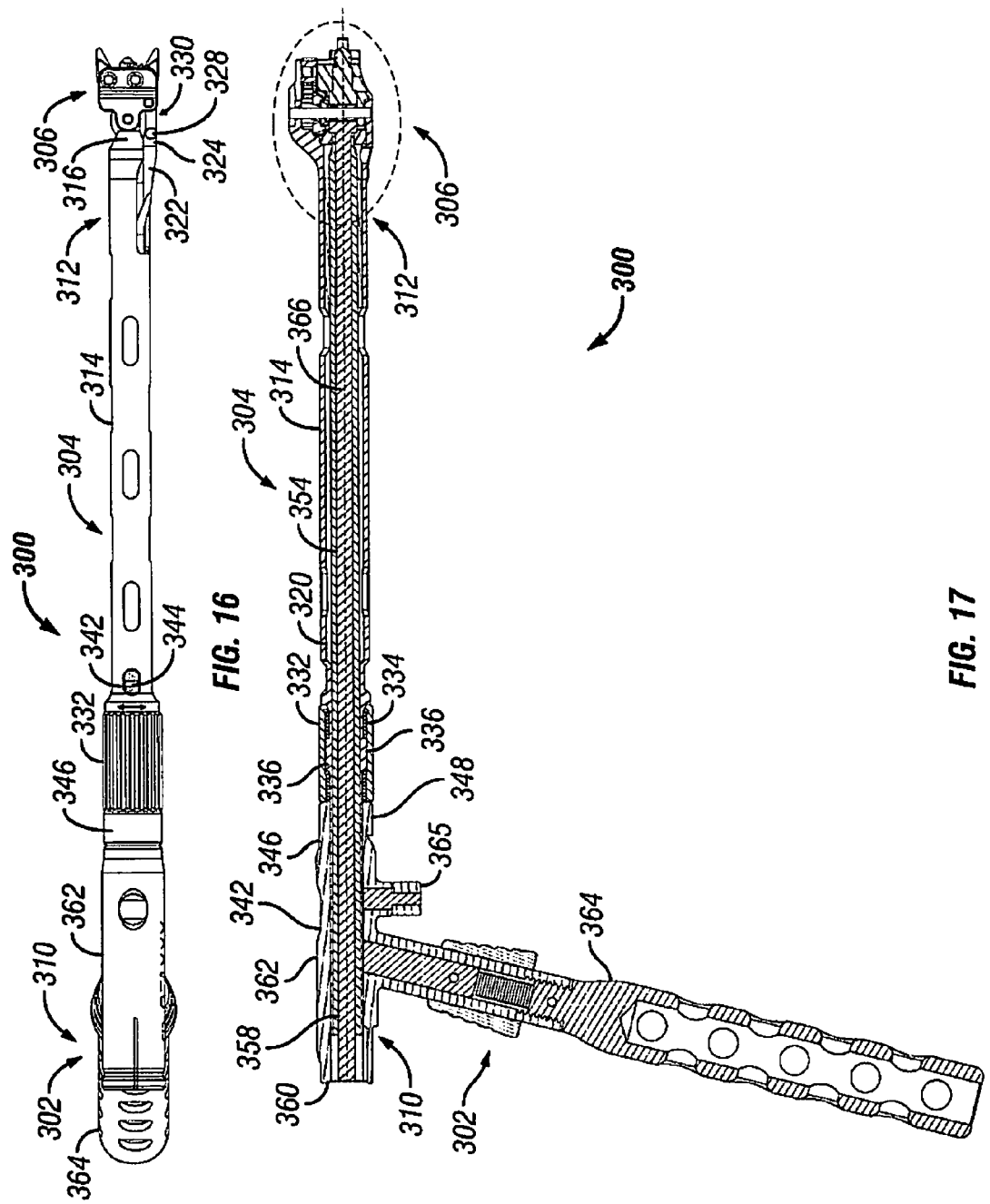

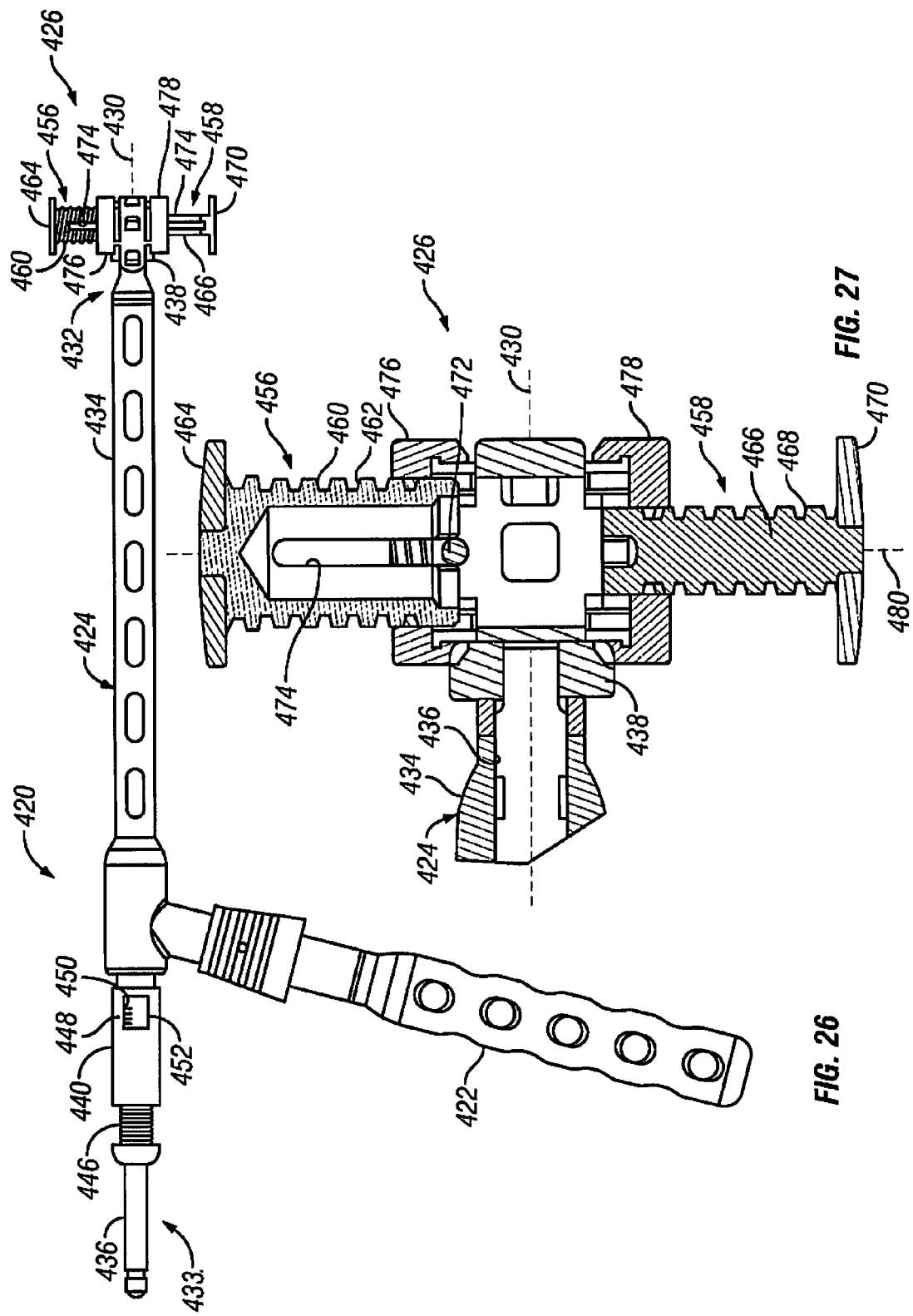

EXPANDABLE TRIAL ASSEMBLY FOR EXPANDABLE VERTEBRAL IMPLANT

CROSS-REFERENCE TO RELATED APPLICATIONS

The present invention is a continuation-in-part of U.S. patent application Ser. No. 13/333,227, entitled "Expandable Vertebral Implant," filed on Dec. 21, 2011, which is a continuation-in-part of U.S. patent application Ser. No. 12/758,529 entitled "Expandable Vertebral Implant" filed on Apr. 12, 2010 now U.S. Pat. No. 8,282,683, the entire disclosure of which is incorporated herein by reference.

FIELD OF THE INVENTION

The present invention relates to a device to support the spine after removal of at least a part of a vertebra.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable implants may be adjusted prior to insertion into the cavity, while others may be adjusted in situ. Two advantages of the vertebral body replacement using an expandable prosthetic device that is adjustable in situ is that it is easy to place or insert and it permits an optimal, tight fit and correction of the deformity by in vivo expansion of the device. Some other advantages offered by an expandable prosthetic device are that they can facilitate distraction across the resected vertebral defect for correction of the deformity, and allow immediate load bearing after corpectomy.

Instrumentation and specialized tools for insertion of a vertebral implant is one important design parameter to consider when designing a vertebral implant. Spinal surgery procedures can present several challenges because of the small clearances around the prosthetic when it is being inserted into position. Another important design consideration includes the ability of the device to accommodate various surgical approaches for insertion of the vertebral implant.

SUMMARY OF THE INVENTION

The present invention relates to an expandable prosthetic implant device for engagement between vertebrae generally comprising an inner member, outer member, and gear member positioned coaxial with respect to each other such that the inner and outer members are moveable relative to each other along an axis. The inner member has a hollow interior portion and a threaded external portion and includes a first end portion configured to engage an endplate which is capable of engaging a first vertebral body. The outer member has a hollow interior portion configured to receive the inner member and includes a second end portion configured to engage an endplate which is capable of engaging a second vertebral body. The gear member is axially fixed to the outer member and freely rotatable with respect to the outer member and the gear member threadedly engages the threaded portion of the inner member.

The implant is configured to engage the vertebrae such that first and second end portions are oriented in a predetermined alignment with respect to the first and second vertebral bodies. The gear member includes teeth extending around the perimeter of the gear member and the teeth are exposed to the exterior and configured to be accessible by a tool member.

The present invention further relates to a method of inserting an implant comprising providing a trial assembly. The method may further comprise positioning the trial assembly between vertebrae in a patient. The method may further comprise rotating a drive shaft of the trial assembly to cause upper and lower gear members of the trial assembly to rotate causing expansion of a tip assembly of the trial assembly. The method may further comprise measuring expansion of the trial assembly with a scale at a proximal end of the trial assembly. The method may further comprise removing the trial assembly from the patient. The method may further comprise positioning an implant between the vertebrae in the patient. The method may further comprise expanding the implant based on the measured expansion of the trial assembly.

BRIEF DESCRIPTION OF THE DRAWINGS

The present invention will be more readily understood with reference to the embodiments thereof illustrated in the attached drawing figures, in which:

FIG. 16 is a top view of the angling inserter tool of FIG. 14;

FIG. 17 is a cross-sectional view of the angling inserter tool of FIG. 14;

FIG. 26 is a view of the expandable trial assembly of FIG. 24 in an expanded position;

FIG. 27 is a cross-sectional view of the expandable tip assembly of the expandable trial assembly of FIG. 24 in an expanded position;

Throughout the drawing figures, it should be understood that like numerals refer to like features and structures.

DETAILED DESCRIPTION OF THE PREFERRED EMBODIMENTS

Figure 1:
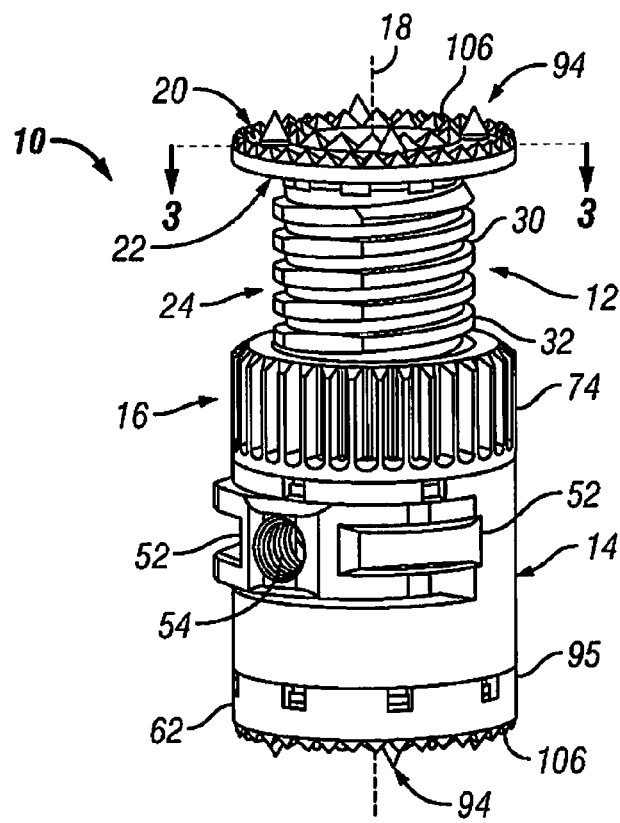
FIG. 1 is a perspective view of an implant in accordance with an embodiment of the present invention.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-6, a preferred embodiment of an expandable vertebral implant 10 is shown. The implant 10 preferably comprises an inner member 12 which may be telescopingly received within an outer member 14. The implant 10 further comprises a gear member 16 generally configured to effect translation of the inner member 12 with respect to the outer member 14 thereby allowing for expansion and contraction of the implant 10. The inner member 12, the outer member 14, and the gear member 16 are preferably centered along a longitudinal axis 18 and define a hollow interior portion which may be filled with bone material, bone growth factors, bone morphogenic proteins, or other materials for encouraging bone growth, blood vessel growth or growth of other tissue through the many apertures in the device. In one preferred embodiment, members 12, 14, and 16 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 12, 14, and 16 may be made of a biologically inert metal alloys, such as titanium, or other suitable materials.

Referring to FIGS. 1-5, the inner member 12 has a generally cylindrical body 24 with a distal end 22 and a proximal end 36. In a preferred embodiment, the body 24 of the inner member 12 comprises an inner surface 28 and an outer surface 30 and generally defines a hollow interior portion 23 extending axially therethrough. At least part of the outer surface 30 preferably includes external threads 32. Located proximate to the distal end 22 of the body 24 are a plurality of tabs 38 which assist in connecting and positionally locating an endplate 20. In a preferred embodiment, the body 24 is configured and dimensioned to be cooperatively received within outer member 14.

Figure 5:
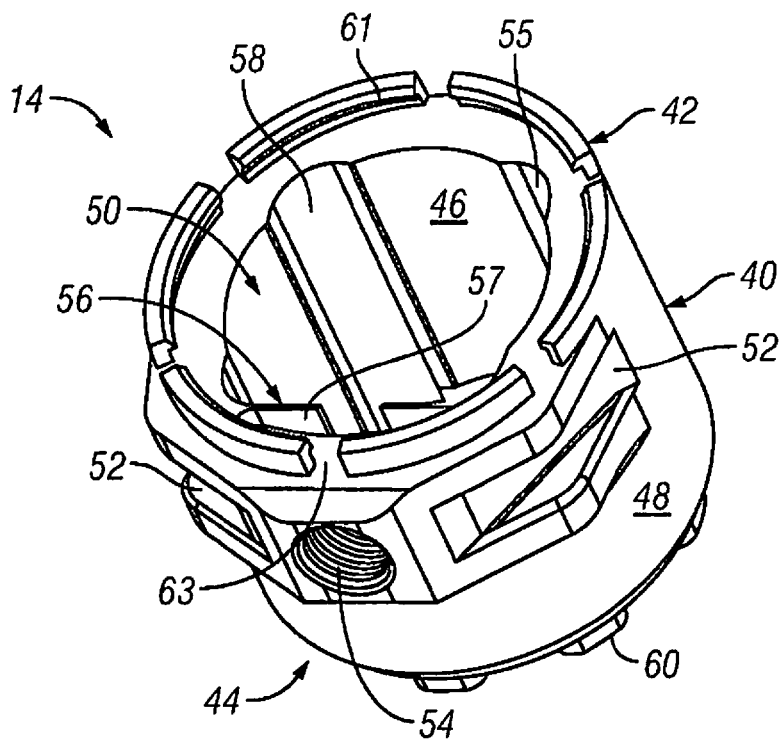
FIG. 5 is perspective view of an embodiment of an outer member of the implant of FIG. 1.

The outer member 14 has a generally cylindrical body 40 with a distal end 42 and a proximal end 44. In a preferred embodiment, the body 40 of the outer member 14 comprises an inner surface 46 and an outer surface 48 and generally defines a hollow interior portion 50 extending axially therethrough. The outer surface 48 preferably has at least one slot 52 and an opening 54 configured and dimensioned to receive a portion of an implantation tool. In a preferred embodiment, the opening 54 extends from the outer surface 48 to the hollow interior portion 50 and at least a portion of the opening 54 is threaded. As best seen in FIG. 5, the inner surface 46 includes a channel 57 for receiving a locking member (discussed below). Located proximate to the proximal end 44 of the outer member 14 are a plurality of tabs 60 which assist in connecting and positionally locating an endplate 62. In a preferred embodiment, a lip 61 is formed around the exterior of the distal end 42 of body 40 and is configured to cooperatively fit with a portion of the gear member 16. A plurality of relief spaces or slots 63 are radially spaced around lip 61 to facilitate a snapping engagement of the lip 61 with the gear member 16. In this regard, slots 63 allow the lip 61 to deform slightly and contract in the radial direction to accommodate gear member 16 to snap on to lip 61. In a preferred embodiment, the interior portion 50 of body 44 is configured and dimensioned to cooperatively receive body 24 of inner member 12 within outer member 14. In this regard, the dimensions of interior portion 50 of body 44 are greater than dimensions of body 24 of inner member 12.

As best seen in FIGS. 2-5, in a preferred embodiment of a prosthetic device 10, the body 24 of the inner member 12 includes a flattened portion 34 which extends at least in part from the distal end 22 to the proximal end 36 and includes a base member 37 having at least one lobe 39 located proximate to the distal end 36 of the body 24. Focusing on FIG. 5, the body 40 of the outer member 14 includes a flattened area 56 and at least one depression 58 on the inner surface 46. When the inner member 12 is assembled within the outer member 14, the flattened area 56 of the outer member 14 cooperatively aligns with the flattened portion 34 of the inner member 12 and the at least one depression 58 of outer member 14 receives the at least one lobe 39 of the inner member 12. The flattened portion 34 and the flattened area 56 along with the lobes 39 and the depressions 58 cooperate to allow the inner member 12 to linearly move with respect to the outer member 14 but prevent the inner member 12 from rotating with respect to the outer member 14. In addition, the base member 37 serves as a stop preventing the inner member 12 from rotating to a point of disengagement from outer member 14.

Figure 6:
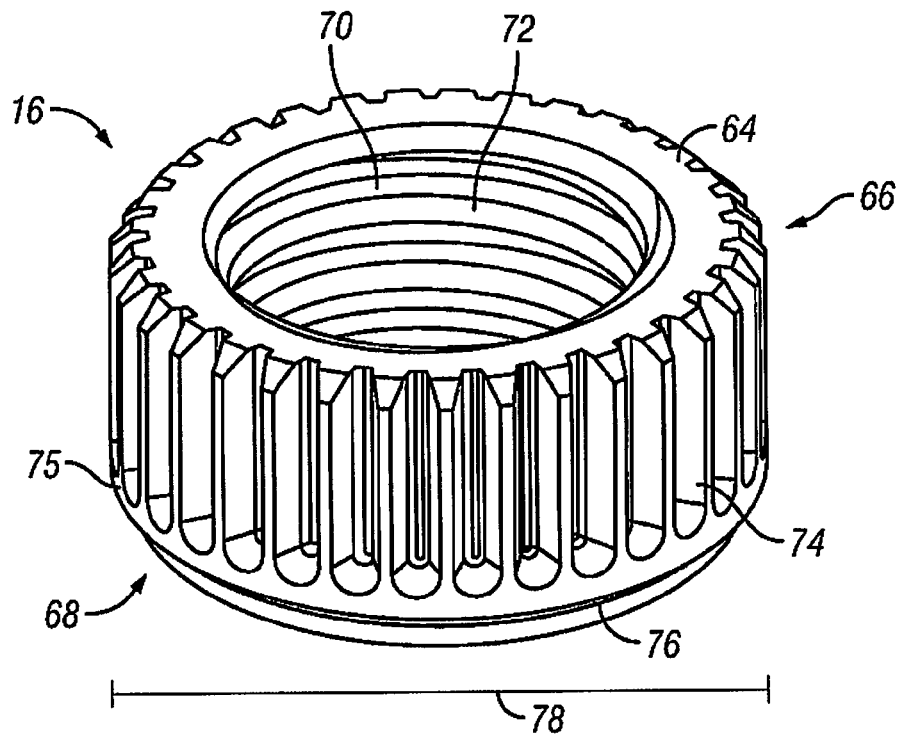
FIG. 6 is an elevated perspective view of one embodiment of a gear member of the implant of FIG. 1.
Figure 7:
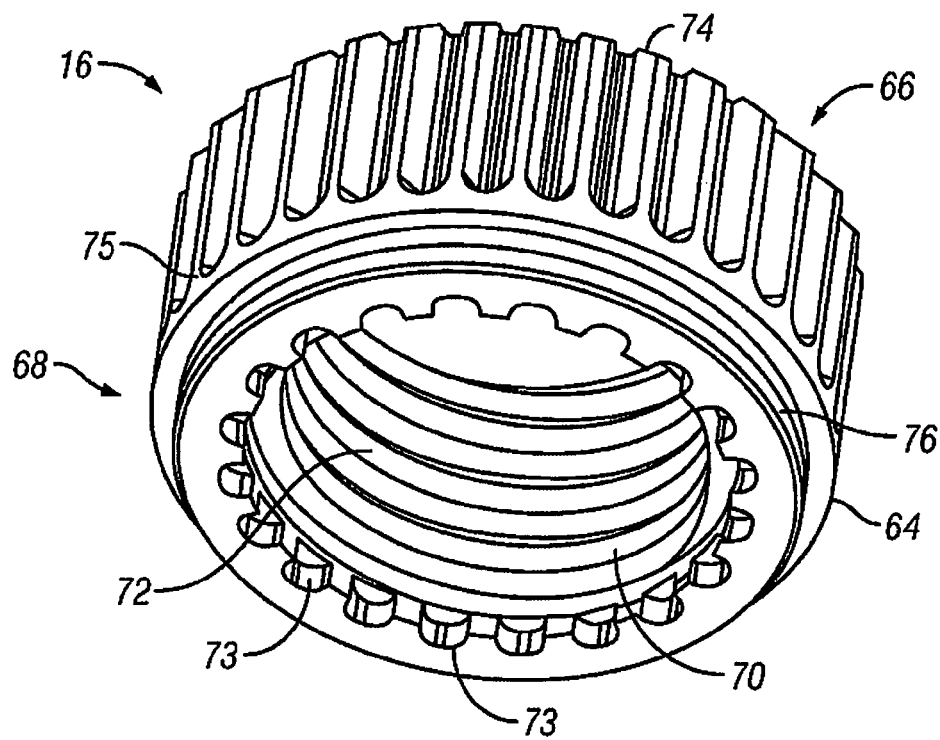
FIG. 7 is a bottom perspective view of the gear member of FIG. 6.

Referring now to FIGS. 6-7, a gear member 16 comprises a generally hollow body 64 extending from a distal end 66 to a proximal end 68 with a helical thread 70 along at least part of an inner wall 72 and an array of gear teeth 74 along a portion of the exterior wall 75. The gear member 16 is generally configured to rotatably connect to the distal end 42 of the outer member 14 and the internal helical thread 70 is configured to engage the external threads 32 of the inner member 12 to cause translation of the inner member 12 with respect to the outer member 14. In a preferred embodiment, the gear member 16 includes a cylindrical cutout feature 76 extending around the inner wall 72 to cooperatively receive the lip 54 of the outer member 14. In this regard, the gear member 16 may rotate freely with respect to the outer member 14 while being retained from longitudinal and lateral movement. In a preferred embodiment, the gear member 16 also includes a series of cutouts 73 located proximate to the proximal end 68 for engaging a portion of a locking member.

With continued reference to FIGS. 6-7, the gear teeth 74 extend substantially from the proximal end 68 to the distal end 66 and extend around the entire periphery of at least a portion of the exterior wall 75. The outer-most external diameter 78 of the gear member 16 is sized to be the same as or slightly smaller than the smallest outer diameter of the endplates 20, 62 and the outer member 14. In this regard, when the implant 10 is viewed from the end in a plane perpendicular to the longitudinal axis 18, the gear member 16 does not protrude radially outward from beyond the perimeter of the endplates 20, 62.

As shown in FIG. 7, in a preferred embodiment, the gear teeth 74 extend a width 80 in a generally radial direction and generally extend radially outward to the outer diameter of the gear member 16. In this regard, the teeth 74 may be designed to have a width 80 to accommodate the expected gear forces given the particular gear ratio, types of material used, and desired overall diameter of prosthetic device 10. One skilled in the art will appreciate that the larger the outer diameter to which the teeth 74 radially extend, the larger the teeth 74 may be designed while still maintaining the same gear ratio. In this regard, when the teeth 74 are made larger, they generally have a better mechanical strength. Also, the ability to design larger, wider, and stronger teeth 74 is advantageous for embodiments where the implant 10 is made of PEEK, other plastic, or other non-metallic materials that may have less mechanical strength than, for instance, titanium.

Furthermore, as described in one embodiment, because the outer-most diameter of the gear member 16 may be as large as the outer diameter of the endplates 20, 62, and the teeth 74 extend radially to the outer-most diameter of the gear member 16, a larger inner diameter of the gear member 16 may be manufactured without compromising mechanical gear strength. As a result, a larger overall inner diameter of the implant 10 may be accommodated which allows the packing of more bone material therein and facilitates bone fusion once the implant 10 is implanted.

Figure 3:
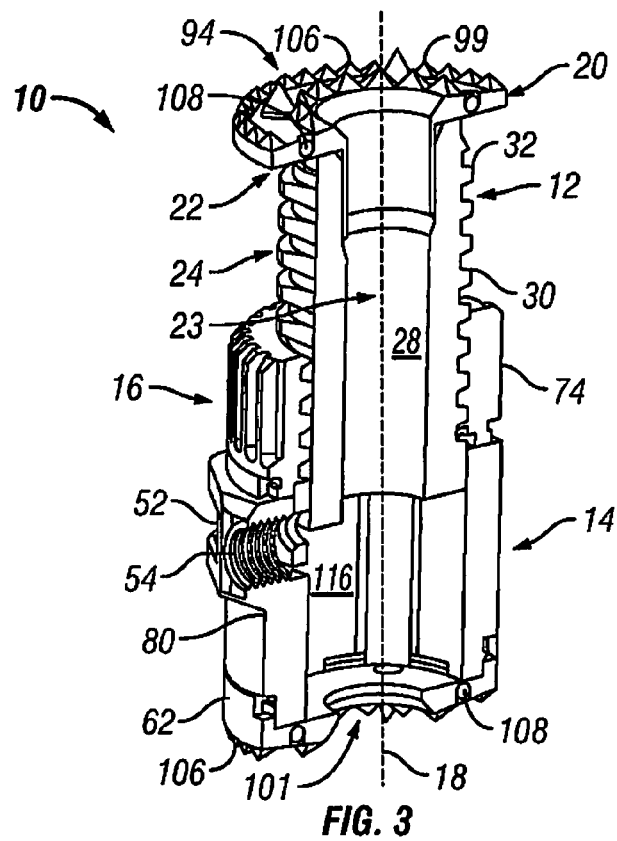
FIG. 3 is a cross-sectional view of the implant of FIG. 1 taken along line 3-3 of FIG. 1.
Figure 2:
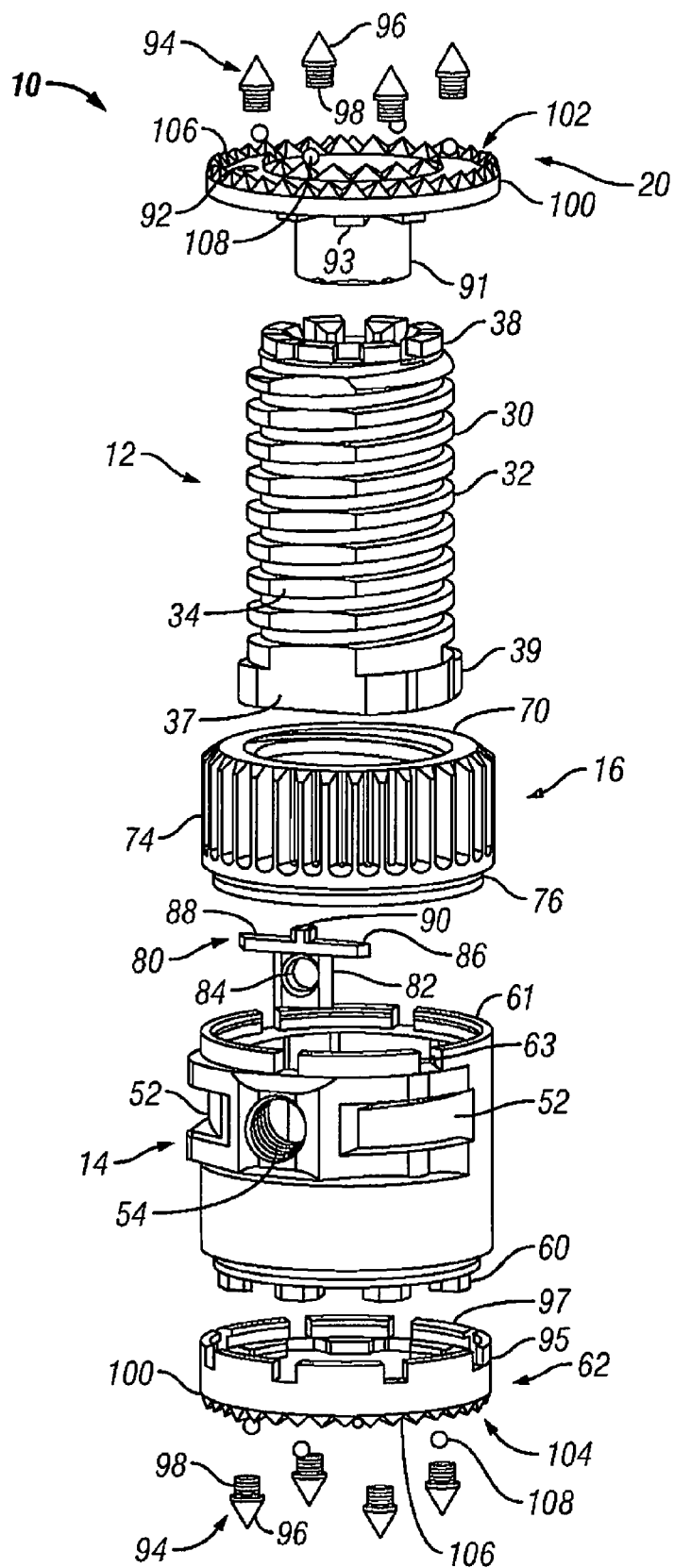
FIG. 2 is an exploded view of the implant of FIG. 1.
Figure 4:
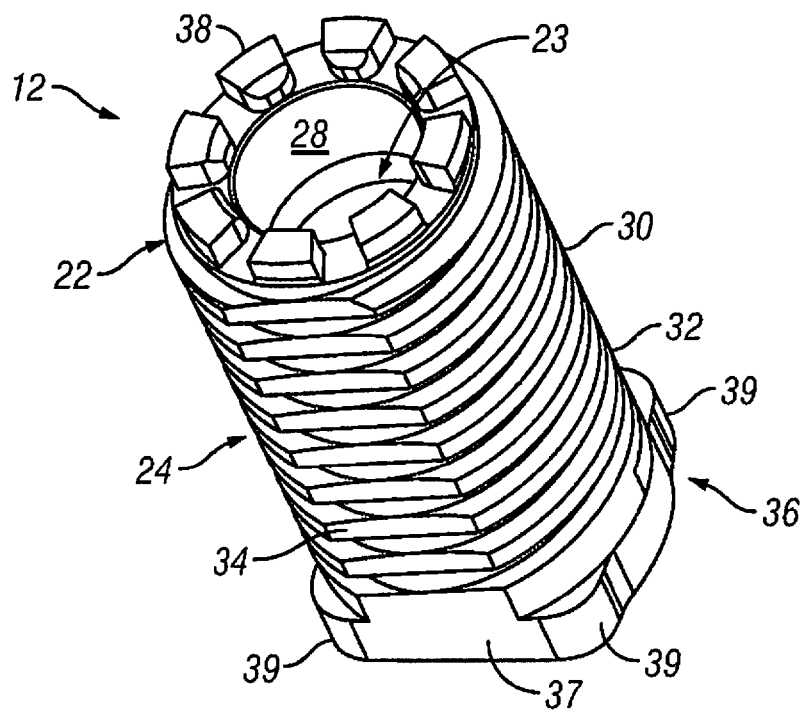
FIG. 4 is perspective view of an embodiment of an inner member of the implant of FIG. 1.

As seen in FIGS. 1-3, in a preferred embodiment, the teeth 74 are exposed to the exterior of prosthetic device 10. Because the teeth 74 are exposed around the periphery, little to no material is needed to cover up the exposed teeth, which generally makes the implant 10 lighter and easier to manufacture than prior art devices that require covering the gear teeth. In addition, the gear member 16 is more easily visible by a surgeon and more readily accessible by a rotation tool than devices that hide or cover gear teeth.

Referring to FIGS. 2, 5, and 7, in a preferred embodiment, the implant 10 also includes a locking member 80. The locking member 80 may be provided to substantially restrict all relative movement between inner member 12 and outer member 14, when, for example, the desired expansion of the prosthetic device 10 has been obtained. The locking member 80 has a body portion 82 with a through-hole 84. In a preferred embodiment, the body portion 82 has at least one, but preferably two, outwardly extending, flexible arms 86, 88 and at least one engagement member 90. In other preferred embodiments, instead of flexible arms 86, 88, it is contemplated that the locking member 80 may include an alternate biasing member, such as a leaf spring. The locking member 80 is configured and dimensioned to be received in the channel 57 of the outer member 14 in such a manner that the arms 86,88 rest against a shelf portion in the channel 57 and the through-hole 84 partially aligns with opening 54. The engagement member 90 preferably protrudes upwardly and is configured and dimensioned to engage the cutouts 73 of the gear member 16 to prevent the gear member 16 from rotating.

Referring now to FIGS. 1-3, in a preferred embodiment, the endplates 20, 62 are shown wherein the endplate 20 connects to the inner member 12 and endplate 62 connects to the outer member 14. In a preferred embodiment, endplate 20 includes an extension portion 91 which is received in the interior portion 23 of inner member 12, for example, in an interference or snap fit and includes a plurality of tabs 93 which interdigitate with tabs 38 to connect and position endplate 20 with respect to the inner member 12. Endplate 62 includes an extension portion 95 which engages the proximal end 44 of the outer member 14, for example, in an interference or snap fit and includes a plurality of tabs 97 which interdigitate with tabs 60 to connect and position endplate 62 with respect to the outer member 14. The endplates 20, 62 also preferably include hollow interior portions 99, 101 which are in fluid communication with the hollow interior portions 23, 50 of inner member 12 and outer member 14, respectively.

In a preferred embodiment, each endplate 20, 62 is generally annular in shape when viewed from the end or perpendicular to the longitudinal axis 18. It is, however, contemplated that the endplates 20, 62 can be other shapes including oblong, elliptical, kidney bean, polygonal, or geometric. Preferably, the endplates 20, 62 are designed to resemble or mimic the footprint of the vertebral body to which the endplates will engage. In this regard, endplates 20, 62 are configured to engage portions of the vertebrae in a predetermined orientation to maximize contact of the superior surface of the endplates 20, 62 with bone.

The dimensions of endplates 20, 62 can be varied to accommodate a patient's anatomy. In some embodiments, the endplates 20, 62 have a wedge-shaped profile to accommodate the natural curvature of the spine. In anatomical terms, the natural curvature of the lumbar spine is referred to as lordosis. When implant 10 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

As shown in FIGS. 1-3, in a preferred embodiment, the endplates 20, 40 include a plurality of mounting holes 92 spaced around the perimeter of each endplate 20, 40 for receiving insertable bone engaging members 94. In one embodiment, bone engaging members 94, comprise conical spikes 96 each having a cylindrical base portion 98 configured to fit within holes 92, for instance, by press-fit or by threaded engagement. In alternate embodiments, differently shaped bone engaging members 100 may be used, or in other embodiments no bone engaging members may be used. Referring again to FIG. 2, according to one embodiment, endplates 20, 62 have chamfered edges 100 around the perimeter to facilitate insertion and/or accommodate the shape of the vertebral bodies which they engage. The superior or bone engaging surfaces 102, 104 of endplates 20, 62 may also include numerous types of texturing to provide better initial stability and/or grasping contact between the end plate and the respective vertebrae. In a preferred embodiment, the texturing is a plurality of teeth 106. In preferred embodiments where the implant 10 is manufactured from PEEK or other plastic materials, the endplates 20, 62 may also include radio-opaque material, such as tantalum markers 108, which aid in providing location markers in radiographic images.

In preferred embodiments, the length, diameter, and shape of prosthetic device 10 may vary to accommodate different applications, different procedures, implantation into different regions of the spine, or size of vertebral body or bodies being replaced or repaired. For example, implant 10 may be expandable to a longer distance to replace multiple vertebral bodies. Also endplates 20, 62 can be sized and shaped as well as positioned to accommodate different procedures and approached to the spine. For example, endplates 20, 62 may be made smaller for smaller statured patients or for smaller regions of the cervical spine. In addition, it is not required that endplates 20, 62 be shaped and sized identically and in alternate embodiments they can be shaped or sized differently than each other and/or include different bone engaging members or texturing.

Figure 8:
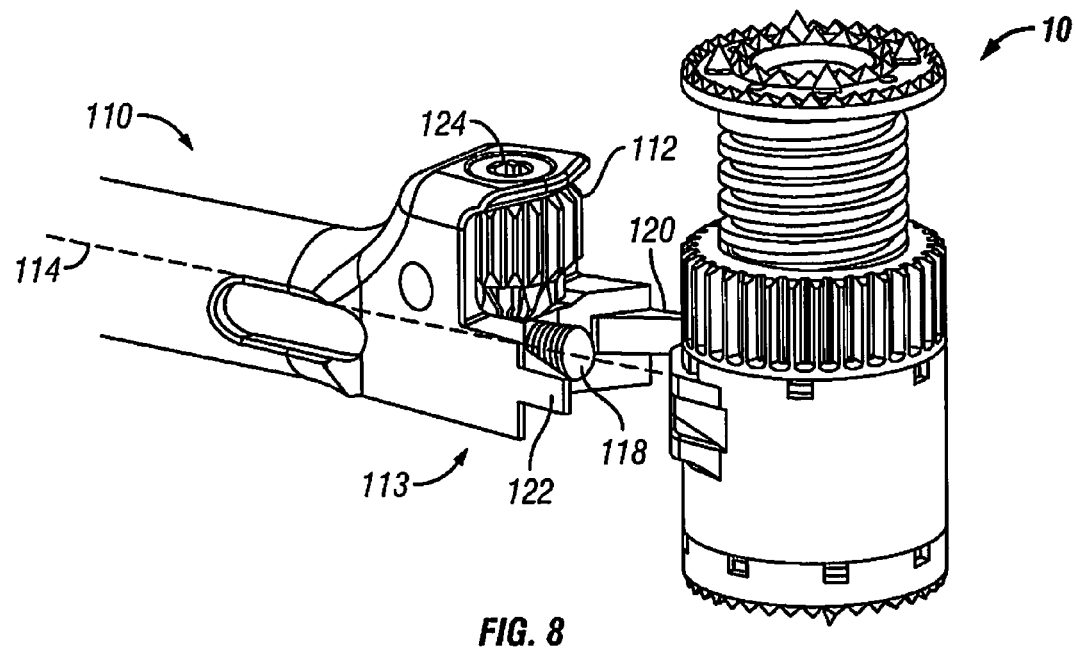
FIG. 8 is a perspective of one embodiment of a tool according to the present invention.
Figure 9:
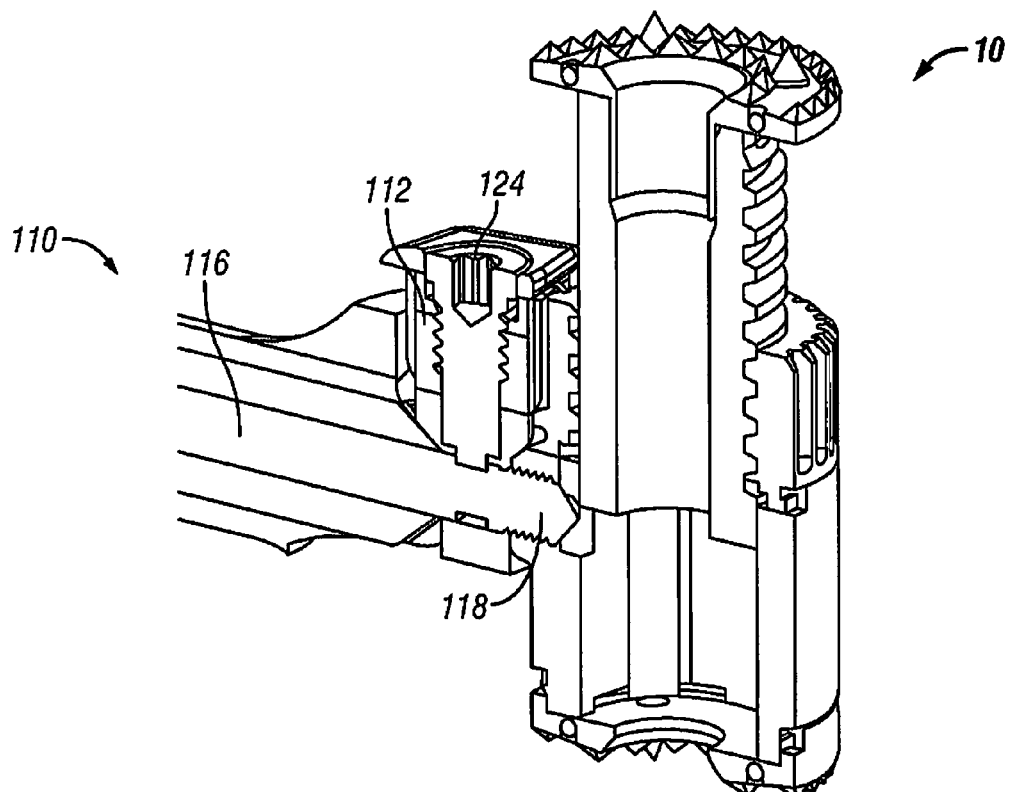
FIG. 9 is a cross-sectional view of the tool of FIG. 8 shown engaging an embodiment of an expandable implant according to the present invention.
Figure 10:
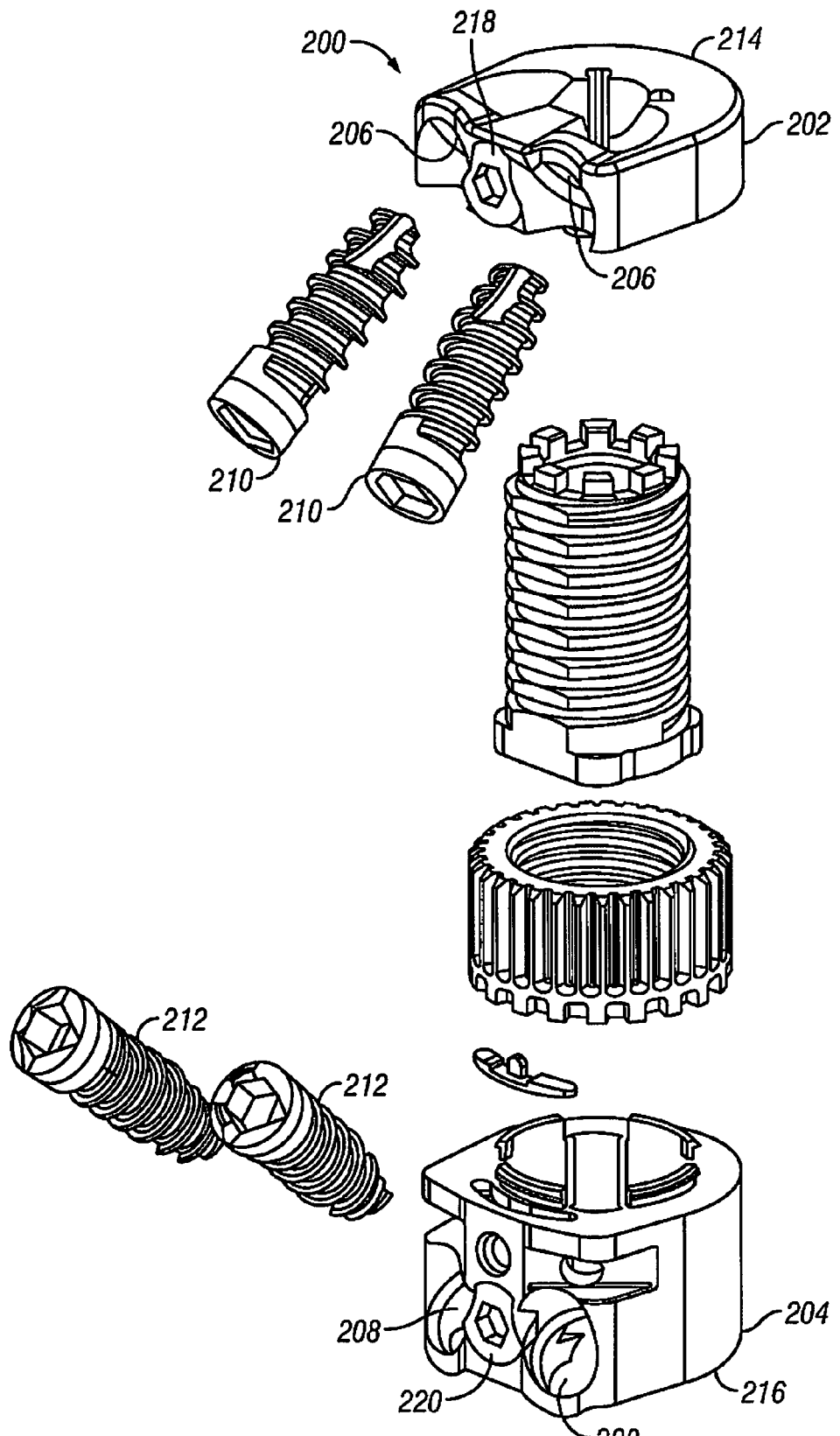
FIG. 10 is a perspective view of another embodiment of an implant according to the present invention.

Turning now to FIGS. 8-9, the implant 10 may be expanded by a tool 110 that includes a gear member 112 at its distal end 113. The tool 110 extends along a tool axis 114 and in operation the tool 110 is configured to engage the implant 10 such that the tool axis 114 is generally perpendicular to the longitudinal axis 18. The gear member 112 is configured to engage teeth 74 of the gear member 16 such that when the gear member 112 is rotated about the axis of the tool 110, the gear member 16 of the implant 10 is rotated about the longitudinal axis 18 and the inner member 12 translates along the longitudinal axis 18 to either expand or contract the implant 10. In a preferred embodiment, the tool 110 may include a central shaft 116 having a threaded distal tip portion 118 that extends distally beyond gear member 112 to facilitate location and mounting of tool 110 with the implant 10. The threaded distal tip portion 118 preferably includes a generally conical end portion and may be configured to extend radially through the opening 54 and threadably engage opening 54 in the outer member 14.

With continued reference to FIGS. 8-9, in one embodiment of prosthetic device 10 at least one, but preferably a plurality of mounting features or slots 52 are provided along the outer surface 48 of outer member 14. The tool 110 includes at least one, but preferably two, articulating arms 120, 122 that engage slots 52 for better engagement of the tool 110 with the implant 10 during insertion of the implant 10. In another preferred embodiment, the tool 110 may include arms 120, 122 that do not articulate.

In an exemplary use of the tool 110 with the implant 10, the tool 110 initially engages the slots 52 of the implant 10 via the arms 120, 122 and gear member 112 engages gear member 16 via their respective interdigitating teeth. A control member on the proximal end of the tool 110 (not shown) is manipulated to advance the central shaft 116 toward opening 54. The threaded tip portion 118 enters into opening 54 engaging the threads in opening 54 as well as engaging the through-hole 84 of locking member 80. It is also contemplated that the central shaft 116 is not movable with respect to the tool 110. In that embodiment, the entire tool 110 is moved so that the central shaft can enter and engage the opening 54 and the through-hole 84. As discussed earlier, the though-hole 84 is offset from opening 54, thus, when threaded tip 118 engages and advances into the opening 54 and the through-hole 84, the locking member 80 is pulled downwardly, riding along the conical edge of the tip 118 until the through-hole 84 is aligned with the opening 54. As the locking member 80 is pulled downwardly, the arms 82, 84 are flexed and the engagement member 90 disengages from the cutout 73 of the gear member 16 allowing the gear member 16 to rotate freely. The gear member 112 of tool 110 is then rotated via opening 114 which, in turn, rotates gear member 16. As discussed above, the rotation of gear member 16 results in the movement of inner member 12 causing the implant 10 to either expand or contract, depending on the direction the gear member 16 is rotated. Once the desired height for implant 10 is achieved, the tool member 110 is disengaged from implant 10. When the tool 110 is removed, the locking member 80 returns to the back to its initial position because of the arms 82, 84 returning back to their unflexed, at-rest state. The initial position of locking member 80 prevents the gear member 16 from turning because of the engagement of engagement member 90 with the cutouts 73. In that regard, implant 10 is locked from movement when the locking member 80 is in its initial position.

The benefit provided by the present locking mechanism is that it allows for a positive lock that engages and disengages automatically with the engagement and disengagement of the tool 110 with the implant 10, which minimizes the steps the surgeon must perform during the procedure.

Referring now to FIGS. 10-13, alternate preferred embodiments of endplates for the expandable implant 10 are shown. Looking at FIG. 10, in one variation, the endplates 202 and outer member 204 each include at least one screw hole 206, 208, but, preferably, each include two screw holes. The screw holes 206, 208 are configured and dimensioned to receive screws 210, 212. In a preferred embodiment, the screw holes 206, 208 are angled such that when the screws 210, 212 are seated in the screw holes 206, 208, the screws 210, 212 will extend outwardly from the superior surface 214 of endplate 202 and inferior surface 216 of outer member 204. Endplate 202 and outer member 204 also preferably include a locking element 218, 220 which, in a first position, allow the screws 210, 212 to back out from the seated position and, in a second position, block the screws 210, 212 from backing out of the seated position. In an exemplary use, once the implant 200 is installed and expanded to the desired position, the screws 210, 212 can be installed through the screw holes 206, 208 in such a manner as to purchase into the adjacent vertebral bodies. Once the screws 210, 212 are properly installed, including being engaged with the adjacent vertebral bodies, the locking elements 218, 220 can be actuated to block the screws 210, 212 from backing out of their installed position. The inclusion of screws 210, 212 in the endplate 202 and the outer member 204 provides for additional fixation of the implant 200 in the intervertebral space.

Figure 11:
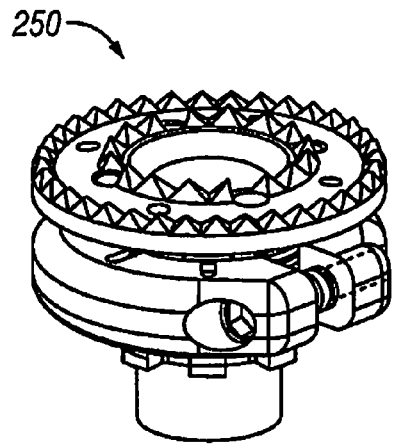
FIG. 11 is a perspective view of another embodiment of an endplate of an implant according to the present invention.
Figure 12:
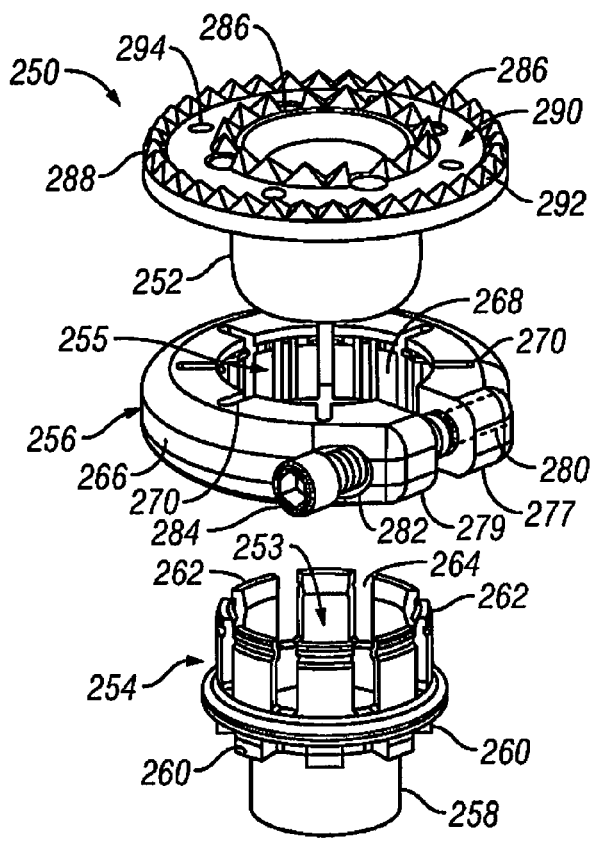
FIG. 12 is an exploded view of the endplate of FIG. 11.
Figure 13:
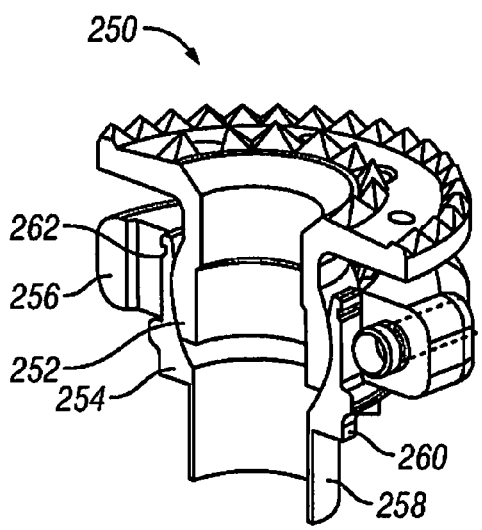
FIG. 13 is a cross-sectional view of the endplate of FIG. 11.

Turning to FIGS. 11-13, another preferred embodiment of an endplate 250 is shown. The endplate 250 is similar to endplate 20 but includes the additional functionality of being poly-axially rotatable with respect to an implant. In a preferred embodiment, endplate 250 includes a generally arcuate extension portion 252 which is received in an interior portion 253 of a receiving member 254 in such a manner as to allow the endplate 250 to move poly-axially with respect to the receiving member 254.

In a preferred embodiment, the receiving member 254 is received in an interior portion 255 of a locking ring 256. The receiving member 254 preferably includes a neck portion 258 as well as a plurality of tabs 260. The neck portion 258 is configured and dimensioned to be received within a hollow interior of an inner member, for example, in an interference or snap fit, and the plurality of tabs 260 interdigitate with tabs to connect and position the receiving member 254 with respect to an inner member. The receiving member 254 further includes a plurality of fingers 262 configured to cooperatively receive the extension portion 252 of endplate 250. A plurality of relief spaces or slots 264 are radially spaced between fingers 262 to allow fingers 262 to bend or flex radially.

In a preferred embodiment, the locking ring 256 has a generally annular, c-shape and includes an exterior wall 266, an interior wall 268, and ends 277, 279. The interior wall 268 preferably defines and interior portion 255. In a preferred embodiment, the interior wall 268 includes a plurality of channel 270 which are spaced radially along the locking ring 256. The channels 270 allow the locking ring 256 to bend or flex radially. The ends 277, 279 each include openings 280, 282 which may be partially threaded. A locking element 284 is configured and dimensioned to be threadingly received in the openings 280, 282. It also contemplated that that locking element 284 can engage the ends 277, 279 by other non-threaded means, such as a sliding fit.

With continued reference to FIGS. 11-13, in a preferred embodiment, the endplate 250 includes a plurality of mounting holes 286 spaced around the perimeter of the endplate 250 for receiving insertable bone engaging members. In one embodiment, bone engaging members, comprise conical spikes each having a cylindrical base portion configured to fit within holes 286, for instance, by press-fit or by threaded engagement. In alternate embodiments, differently shaped bone engaging members may be used, or in other embodiments no bone engaging members may be used. According to one preferred embodiment, endplate 250 has chamfered edges 288 around the perimeter to facilitate insertion and/or accommodate the shape of the vertebral bodies which they engage. The superior or bone engaging surfaces 290 of endplate 250 may also include numerous types of texturing to provide better initial stability and/or grasping contact between the end plate and the respective vertebrae. In a preferred embodiment, the texturing is a plurality of teeth 292. In preferred embodiments where the implant is manufactured from PEEK or other plastic materials, the endplate 250 may also include radio-opaque material, such as tantalum markers 294, which aid in providing location markers in radiographic images.

In an exemplary use, during the implant installation and expansion to the desired position, the endplate 250 can move in poly-axial fashion with respect to the implant to accommodate the anatomy of the adjacent vertebral body as well as accommodate the natural curvature of the spine, such as kyphosis and lordosis. More specifically, the arcuate extension portion 252 is free to move in the interior portion 253 of the receiving portion 254. The fingers 262 are generally compliant and can flex to accommodate the movement of the arcuate extension portion 252. Once the desired positioning of the endplate 250 is achieved, the endplate 250 can be locked in place. The endplate 250 is locked in place by actuating the locking element 284. As the element 284 engages the threading in opening 280,282 the ends 277, 279 of the locking ring 256 are brought closer together contracting the ring 254 and reducing the size of the interior portion 255. As the ring 254 contracts, the fingers 262 of the receiving member 254, abutting against the inner wall 268, are flexed radially inwardly pushing against the extension portion 252. As a result, the endplate 250 is locked in place.

Figure 14:
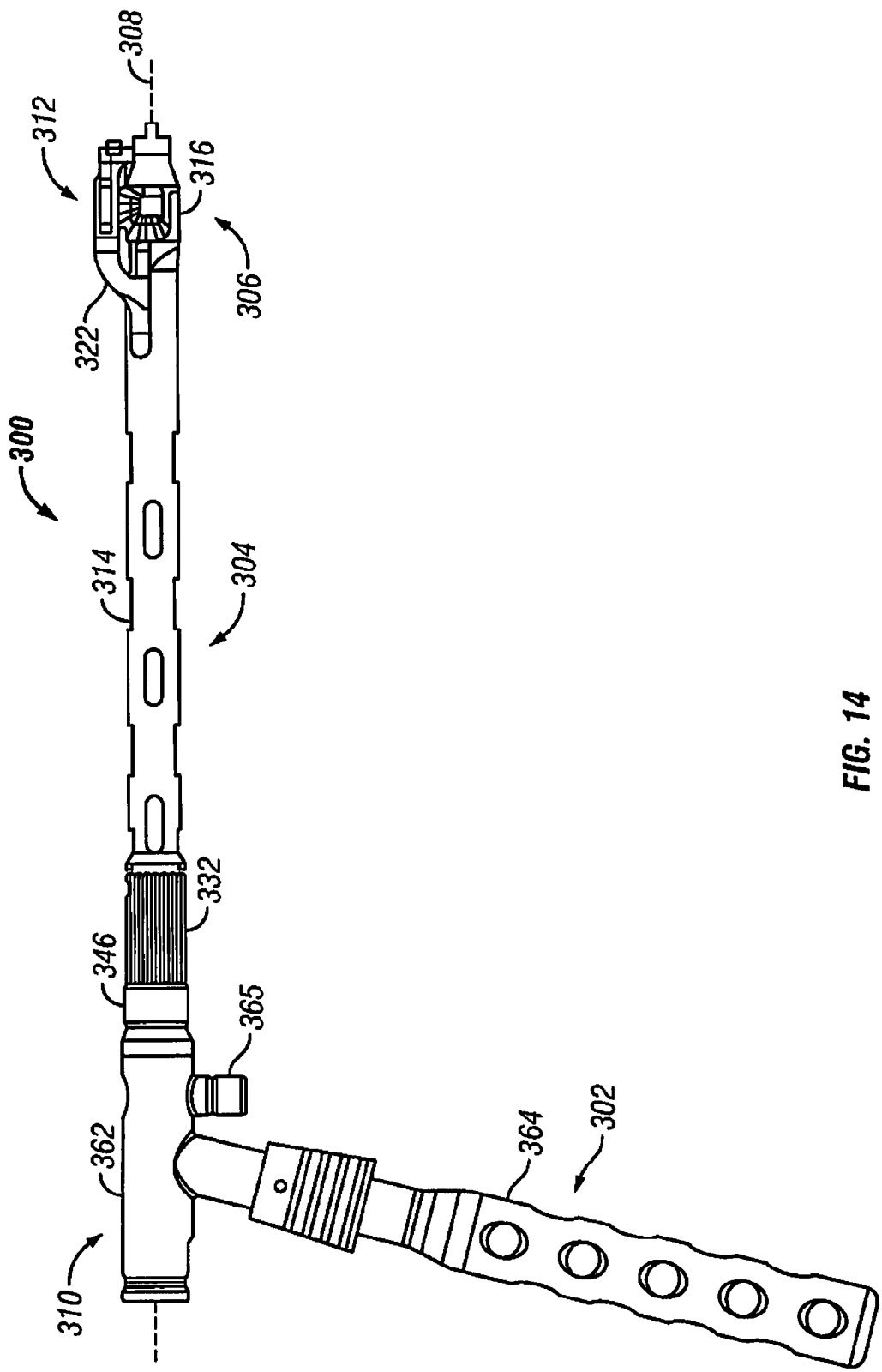
FIG. 14 is a perspective view of an angling inserter tool of one embodiment of the present invention.
Figure 18:
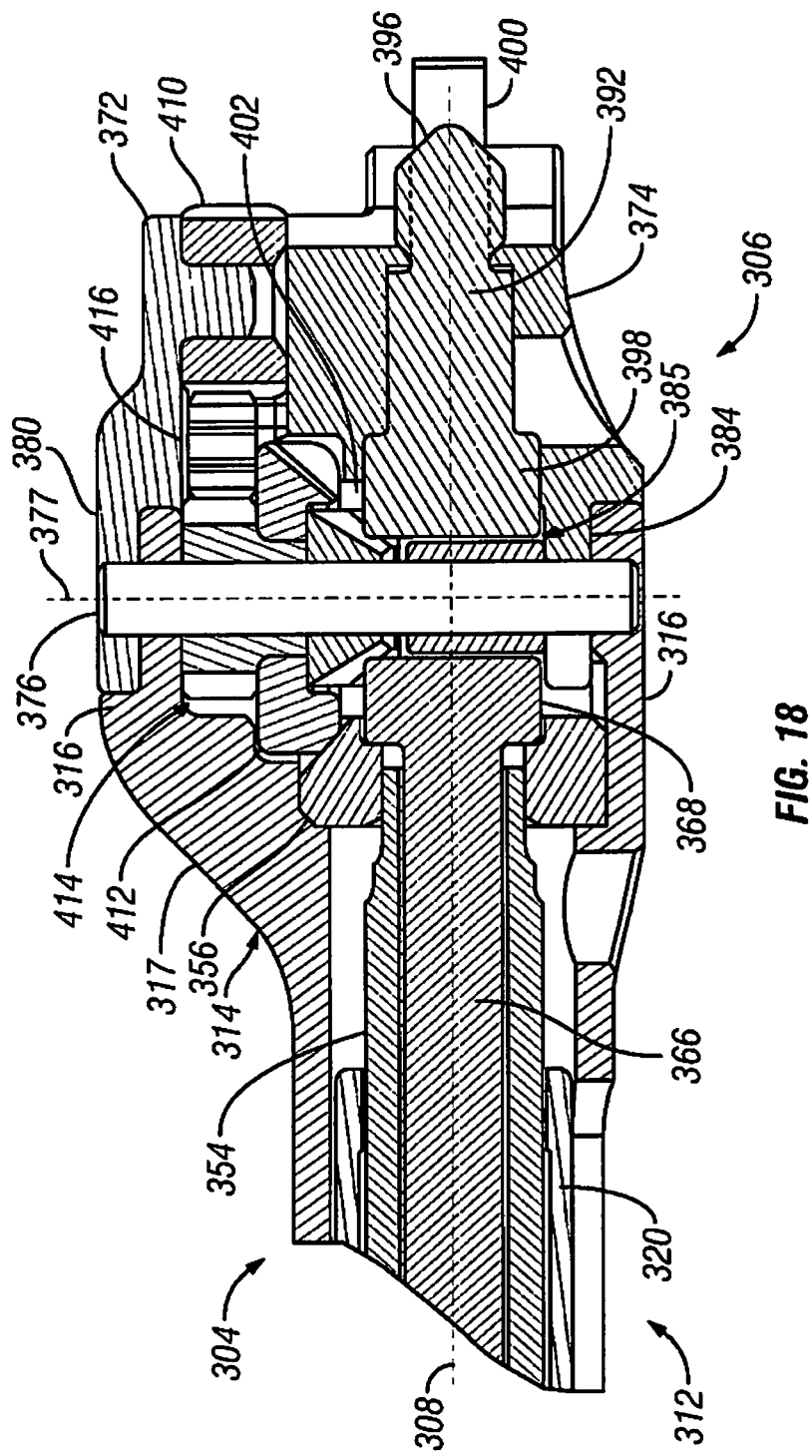
FIG. 18 is a cross-sectional view of one embodiment of a tip assembly of the angling inserter tool of FIG. 14.
Figure 19:
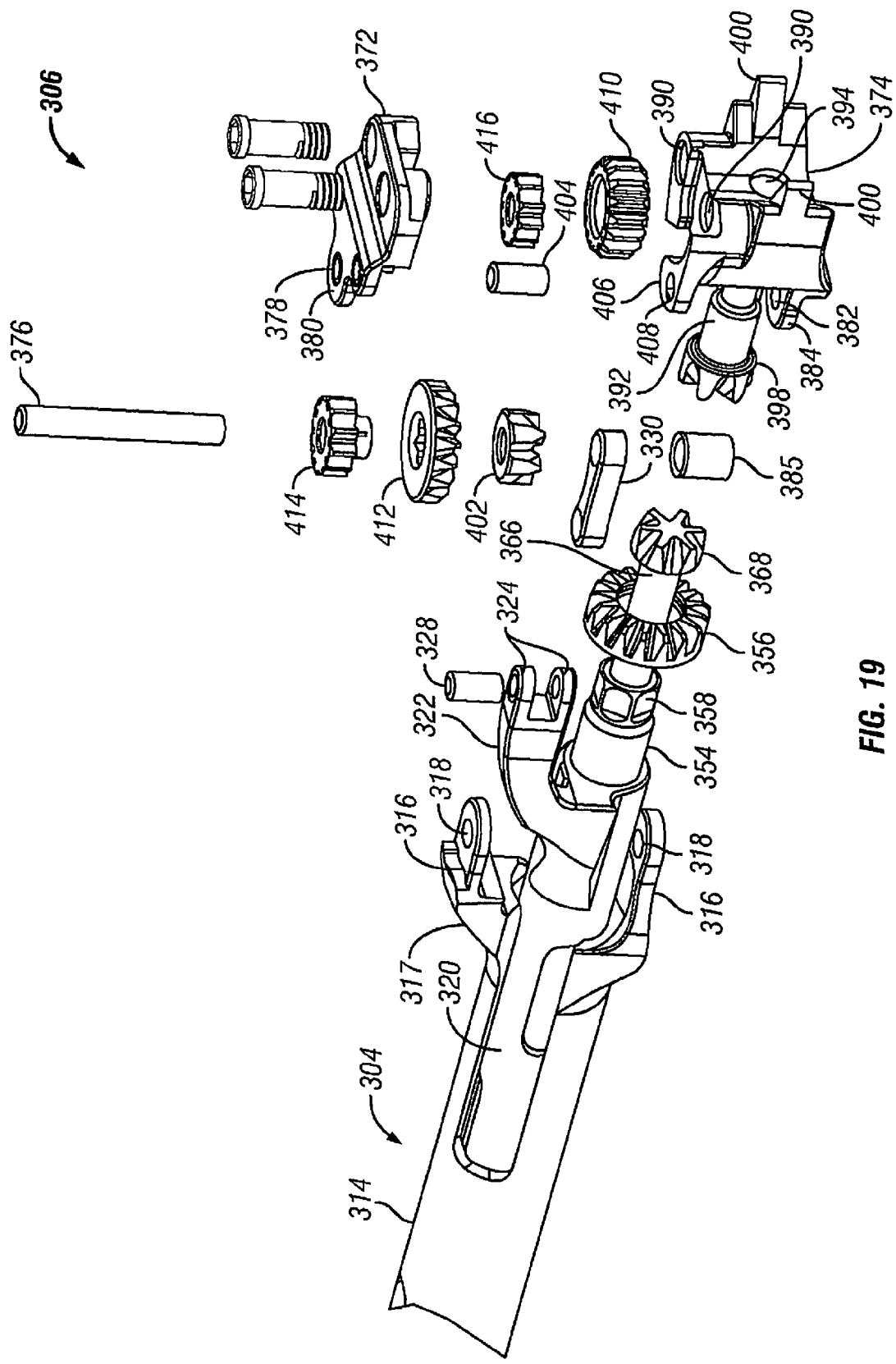
FIG. 19 is an exploded view of the tip assembly of FIG. 18.

Referring now to FIGS. 14-19, an angling inserter tool 300 is shown that may be used to expand the implant 10 in accordance with embodiments of the present invention. The tool 300 is configured to hold the implant 10. As illustrated, the angling inserter tool 300 may comprise a handle portion 302, a cylindrical base portion 304, and a tip assembly 306. In preferred embodiments, the cylindrical base portion 304 is disposed between the handle portion 302 and the tip assembly 306. As best seen in FIG. 14, the angling inserter tool 300 has a longitudinal or tool axis 308 that passes through the tool 300 from proximal end 310 to distal end 312. The tip assembly 306 can be angled relative to the tool axis 308, for example, allowing the implant to be placed around or behind certain anatomical structures. As best seen in FIGS. 18 and 19, the tool 300 includes a primary gear mechanism (e.g., gears 356, 410, 412, 414, 416), for example, configured to drive gear member 16 on the implant 10 it holds, and the tool 300 also includes a second gear mechanism (e.g., distal gear 368, central gear 402, proximal gear portion 398), for example, configured to attached or release the implant 10 from the tool 300.

In some embodiments, the cylindrical base portion 304 includes an outer cylinder 314. At distal end 312, the outer cylinder 314 preferably includes arms 316 that extend distally from the outer cylinder 314, as best seen in FIGS. 18 and 19. One of the arms 316 may include a bent portion 317 at least a portion of which extends radially outward from the outer cylinder 314. Each of the arms may include an opening 318. The openings 318 in each of the arms 316 may be axially aligned and configured to receive a pin 376, as best seen in FIGS. 18 and 19. The pin 376 may rotatably secure the tip assembly 306 to the cylindrical base portion 304 allowing the tip assembly 306 to angulate with respect to the tool axis 308.

Referring to FIGS. 15-19, in some embodiments, the cylindrical base portion 304 also includes an internal shaft 320. As illustrated, the internal shaft 320 may be coaxial with the outer cylinder 314 wherein the internal shaft 320 is received within the outer cylinder 314. In preferred embodiments, the internal shaft 320 is a generally cylindrical body. In present embodiments, the internal shaft 320 can translate longitudinally with respect to the outer cylinder 314. In a preferred embodiment, the internal shaft 320 has an angulated distal end 322, which may be offset from tool axis 308. As best seen in FIG. 19, the angulated distal end 322 may include tabs 324 which may each include an opening 326. The openings 326 in each of the tabs 324 may be axially aligned and configured to receive a pin 328 as shown on FIG. 19. The pin 328 may secure the internal shaft 320 to a linking arm 330 coupling the tip assembly 306 to the internal shaft 320.

Figure 15:
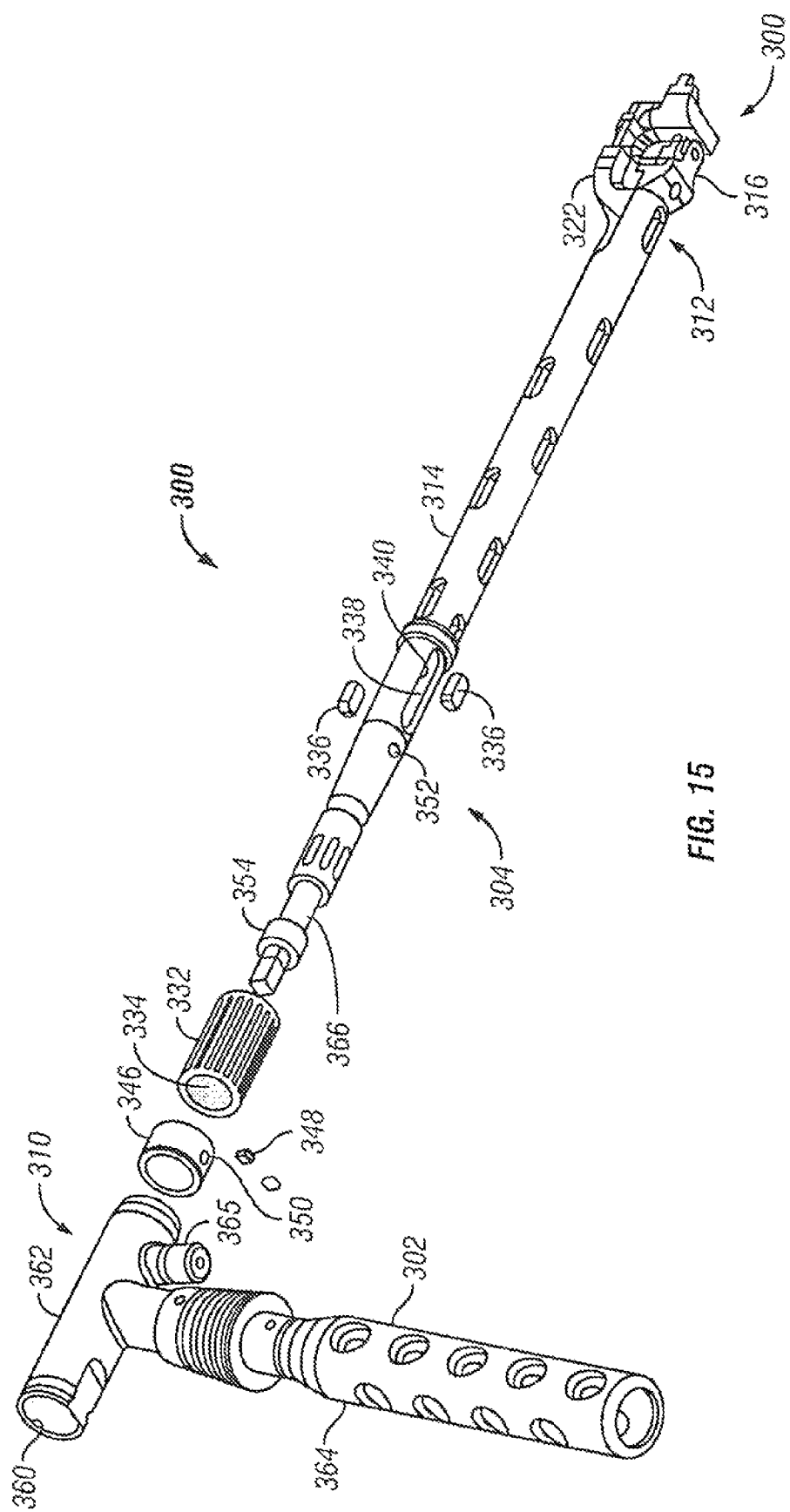
FIG. 15 is an exploded view of the angling inserter tool of FIG. 14.
Figures 22, 23:
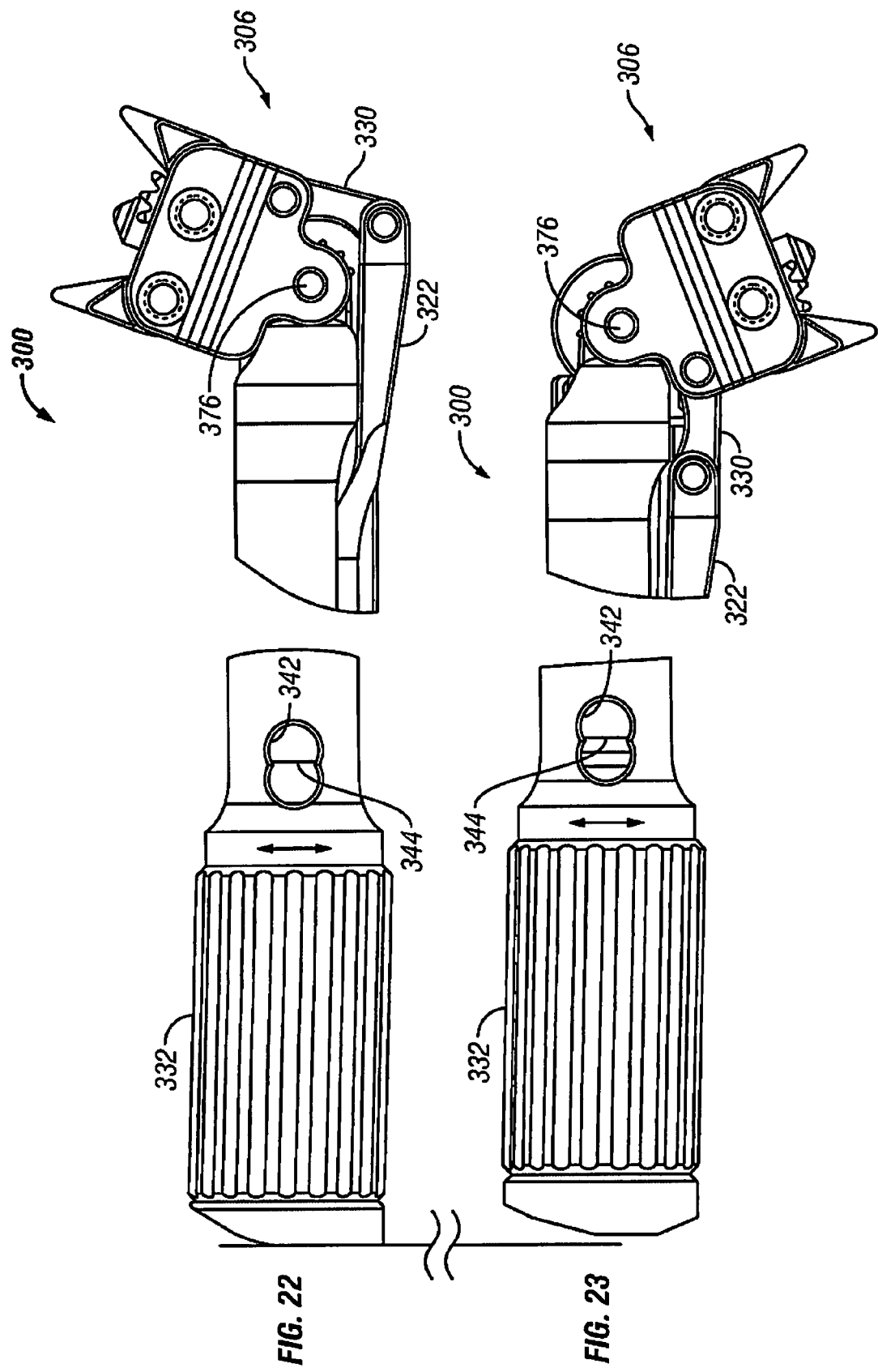
FIGS. 22 and 23 are top views of one embodiment of the angling inserter tool of FIG. 14 showing angulation of the tip assembly.

With reference now to FIGS. 14-17, embodiments of the cylindrical base portion 304 also include a knob 332 generally configured to effect translation of the internal shaft 320 with respect to the outer cylinder 314. In the illustrated embodiment, the knob 332 is disposed on the outer cylinder 314. At least a part of the knob 332 may include internal threads 334, as best seen in FIG. 15. In a preferred embodiment, the internal threads 334 engage one or more blocks 336, as best seen in FIGS. 15 and 17. With continued reference to FIGS. 15 and 17, the blocks 336 are received in one or more openings 338 in the internal shaft 320 and extend through one or more windows 340 in the outer cylinder 314 to engage the internal threads 334 of the knob 332. As illustrated, the windows 340 in the outer cylinder 314 may be longer than the blocks 336, allowing the blocks 336 to move longitudinally in the windows 340. Accordingly, rotation of the knob 332 on the outer cylinder 314 should cause the blocks 336 to move thereby causing the internal shaft 320 to translate within the outer cylinder 314. The internal shaft 320 may extend through the outer cylinder 314 or retract into the outer cylinder 314, depending for example on the direction of the rotation of the knob 332. Because the linking arm 330 couples the internal shaft 320 to the tip assembly 306, translation of the internal shaft 320 should move the tip assembly 306 causing rotation of the tip assembly about the pin 376, as best seen in FIGS. 22 and 23. Accordingly, rotation of the knob 332 on the outer cylinder 314 should cause the blocks 336 to move thereby causing the internal shaft 320 to translate within the outer cylinder 314. The internal shaft 320 may extend through the outer cylinder 314 or retract into the outer cylinder 314, depending for example on the direction of the rotation of the knob 332. Referring now to FIGS. 22 and 23, because the linking arm 330 couples the internal shaft 320 to the tip assembly 306, translation of the internal shaft 320 should move the tip assembly 306 causing rotation of the tip assembly 306 about the pin 376. For example, advancement of the internal shaft 320 through the outer cylinder 314 should effect rotation of the tip assembly 306 about the pin 376 in a first direction (as best seen in FIG. 22), while retraction of the internal shaft into the outer cylinder 314 should effect rotation of the tip assembly 306 about the pin 376 in an opposite direction (as best seen in FIG. 23). Rotation of the tip assembly 306 may be monitored using viewing window 342 and visual indicators 344. As illustrated by FIGS. 22 and 23, visual indicators 344 may be disposed on the internal shaft 320. The visual indicators 344 may be markings, such as numbers, etchings, lines, combinations thereof, or the like, that provide a visual indication of the degree of rotation. The visual indicators 344 on the internal shaft 320 may generally aligned with a viewing window 342 in the outer cylinder 314. The visual indicators 344 should allow accurate measurement of the angulation of the tip assembly 306 even when the tip assembly 306 itself may be obscured from viewing.

With continued to reference to FIGS. 14-17, ring 346 may secure the knob 332 on the outer cylinder 314 in accordance with embodiments of the present invention. As illustrated, the ring 346 may be disposed on the outer cylinder 314 proximally to the knob 332. A set screw 348 disposed through opening 350 in the ring 346 may engage opening 352 in the outer cylinder 314 to secure the ring 346 on the outer cylinder 314.

Referring to FIGS. 15 and 17-19, embodiments of the cylindrical base portion 304 also include a primary drive shaft 354. As illustrated, the primary drive shaft 354 may be coaxial with the internal shaft 320 wherein the primary drive shaft 354 is receiving within the internal shaft 320. In preferred embodiments, the primary drive shaft 354 may be a generally cylindrical body. As best seen on FIGS. 18 and 19, the primary drive shaft 354 includes a distal gear 356, which may be a bevel gear, for example. In certain embodiments, the distal gear 356 is configured to fixedly engage distal end 358 of the primary drive shaft 354, as best seen in FIG. 19. In present embodiments, the primary drive shaft 354 may be configured to rotate with respect to the internal shaft 320. A driving instrument (not shown) may be used to rotate the primary drive shaft 354. The driving instrument may engage the primary drive shaft 354 at proximal end 310 through opening 360 of handle portion 302, as best seen in FIG. 15. As will be discussed in more detail below, the distal gear 356 may be configured to engage one or more corresponding gears (e.g., gears 412, 414, 416) in the tip assembly 306 to cause rotation of implant engagement gear 410 (see, e.g., FIGS. 18 and 19).

In some embodiments, the cylindrical base portion 304 also includes a secondary drive shaft 366. As illustrated, the secondary drive shaft 366 may be coaxial with the primary drive shaft 354 wherein the secondary drive shaft 366 is received the primary drive shaft 354. As best seen in FIGS. 18 and 19, the secondary drive shaft 366 includes a gear 368 at distal end 312, which may be a bevel gear, for example. In present embodiments, the secondary drive shaft 366 may be configured to rotate with respect to the primary drive shaft 354. A driving instrument (not shown) may be used to rotate the secondary drive shaft 366. The driving instrument may engage the secondary drive shaft 366 at the proximal end 310 through the opening 360 in the handle portion, as best seen in FIG. 15. As will be discussed in more detail below, the gear 368 may be configured to engage one or more corresponding gears (e.g., gear 402, gear portion 398) in the tip assembly 306 to cause extension of central shaft 392 (see, e.g., FIGS. 18 and 19).

Referring to FIGS. 14-17, the handle portion 302 includes a cylindrical portion 362 and a handle 364. As illustrated, the handle 364 may preferably extend downward from the cylindrical portion 362. Opening 360 may be disposed in the handle portion 302 at the proximal end 310 so that the secondary drive shaft 366 and the primary drive shaft 354 can be accessed. At least a portion of the cylindrical base portion 304 may be disposed in the cylindrical portion 362. As best seen in FIG. 17, a locking member 365 may engage the outer cylinder 314 of the cylindrical base portion 304 to secure the cylindrical base portion 304 to the handle portion 302. The locking member 365 may extend through an opening in the cylindrical portion 362.

Referring to FIGS. 18-21, the tip assembly 306 will now be described in more detail in accordance with embodiments of the present invention. In preferred embodiments, the tip assembly 306 includes an upper plate 372 and a base portion 374. The upper plate 372 and the base portion 374 may be secured to one another by one or more pins 388. In the illustrated embodiment, two pins 388 are used to secure the upper plate 372 and the base portion 374. As illustrated, the pins 388 may be configured to be received in openings 386 in the upper plate 372 and openings 390 in the base portion 374.

Figure 20:
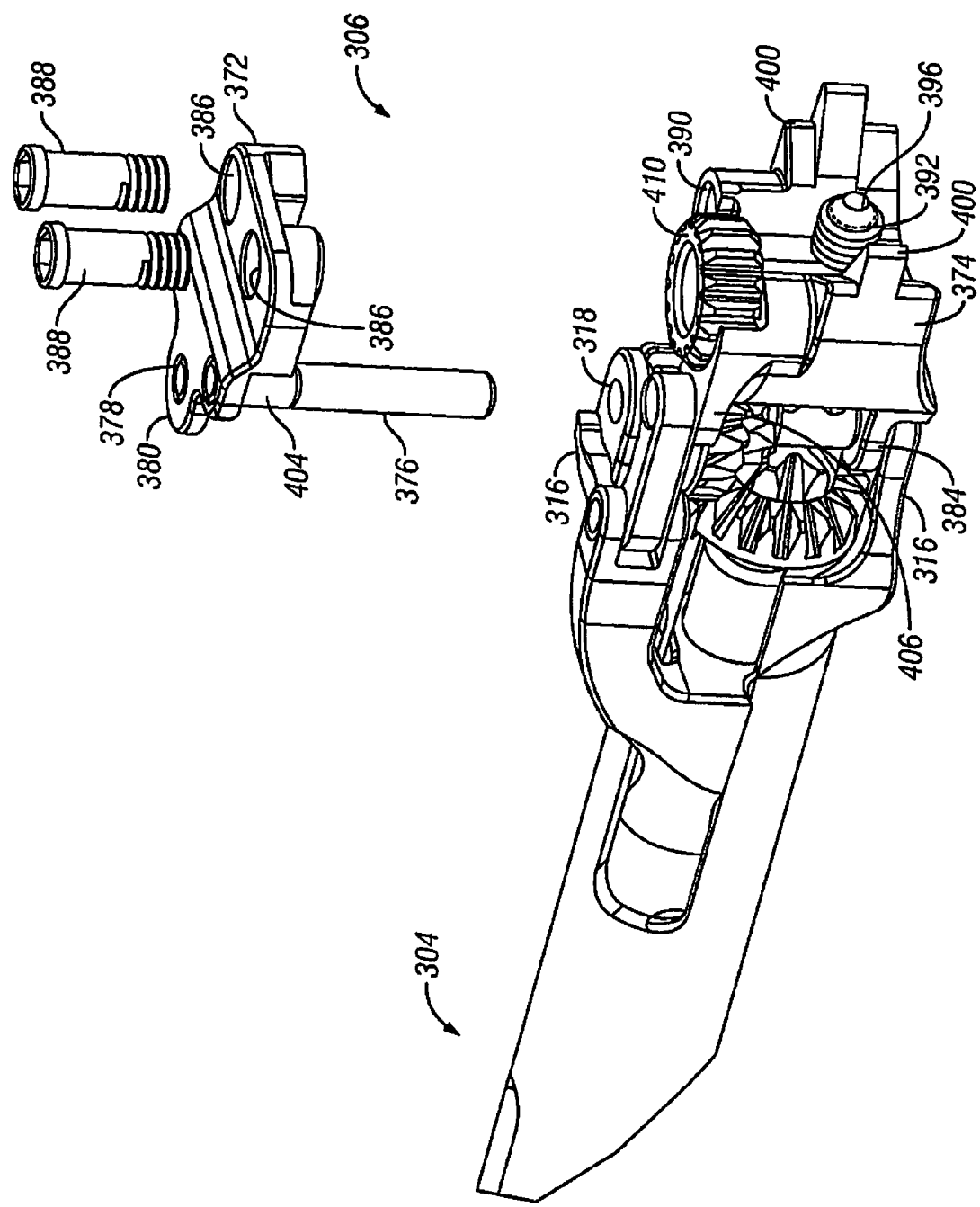
FIG. 20 is an elevated partial exploded view of the tip assembly of FIG. 18.
Figure 21:
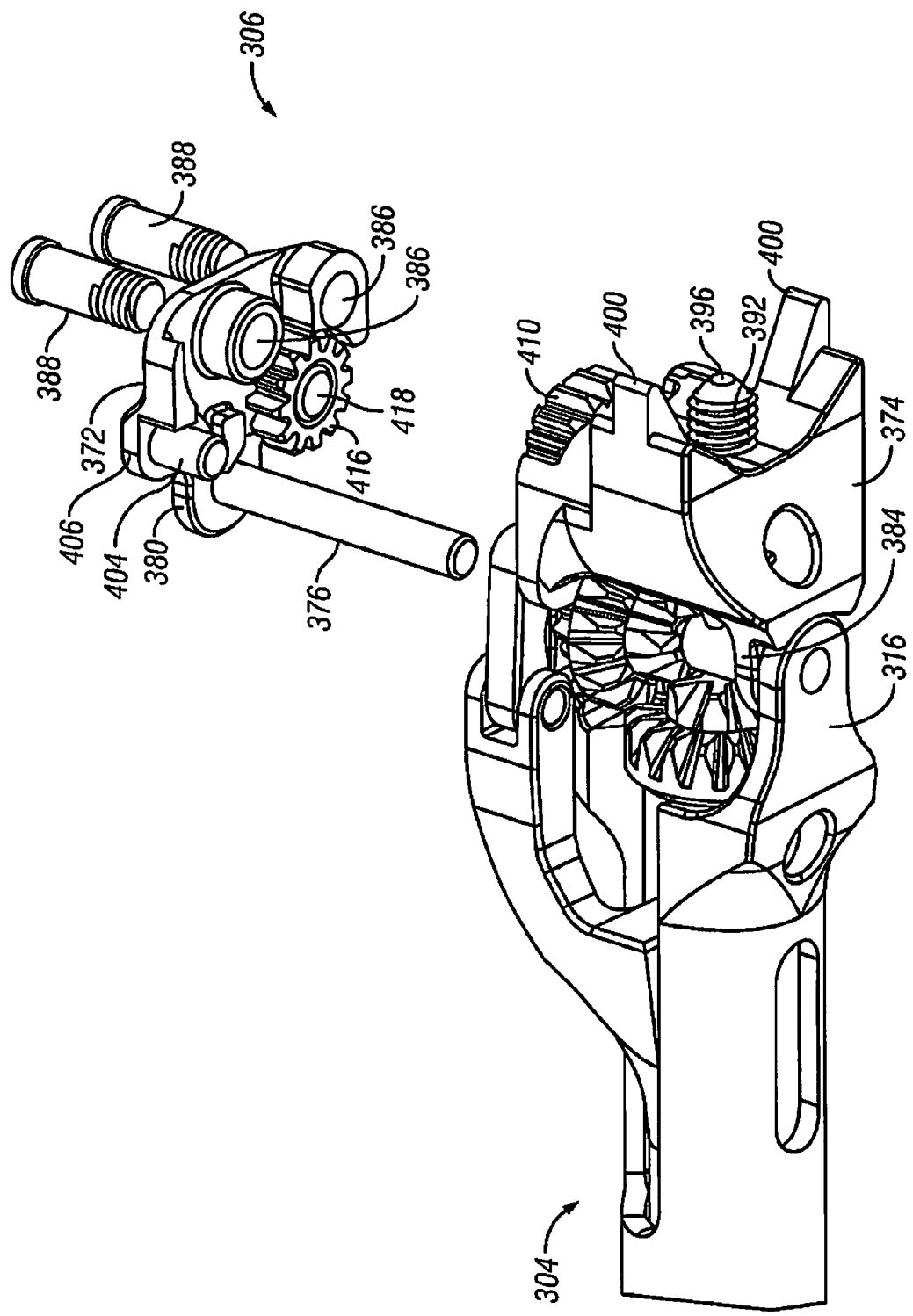
FIG. 21 is another partial exploded view of the tip assembly of FIG. 18.

As previously described, the tip assembly 306 may be rotatably secured to the cylindrical base portion 304 with the pin 376. In the illustrated embodiment, the pin 376 is received in an opening 378 in upper tab 380 of the upper plate 372 and in opening 382 in lower tab 384 of the base portion 374. A bushing 385 may be disposed about at least a portion of the pin 376. The pin 376 has a pin axis 377 (as shown on FIG. 18) about which the tip assembly 306 may rotate. Referring to FIGS. 19-21, the base portion 374 may further include an outer tab 406 having a corresponding opening 408. The outer tab 406 may be offset from the tool axis 308 and configured to receive the pin 404. The pin 404 may secure the tip assembly 306 to the linking arm 330 coupling the tip assembly 306 to the internal shaft 320. Accordingly, advancement or retraction of the internal shaft 320 should cause rotation of the tip assembly 306 about the pin axis 377.

As illustrated by FIGS. 18-21, the tip assembly 306 preferably further includes a central shaft 392 disposed in through-bore 394 (as best seen on FIG. 19) in the base portion 374. The central shaft 392 preferably may include a threaded distal tip portion 396 that extends distally beyond the implant engagement gear 410 to facilitate location and mounting of the angling inserter tool 300 with the implant 10 (see, e.g., FIG. 2) in accordance with embodiments of the present invention. The central shaft 392 may also include a proximal gear portion 398 that engages corresponding gears to facilitate extension of the central shaft 392 through the through-bore 394. For example, as best seen on FIGS. 18 and 19, the proximal gear portion 398 may engage a secondary central gear 402, which may be a bevel gear. The secondary central gear 402 may be disposed about the pin 376 and rotate about the pin axis 377. The secondary central gear 402 may engage gear 368 on the secondary drive shaft 366 of the cylindrical base portion 304. Accordingly, rotation of the secondary drive shaft 366 about the tool axis 308 should cause rotation of the secondary central gear 402 about the pin axis 377 which should in turn drive the proximal gear portion 398 causing rotation of the central shaft 392 and movement of the central shaft through the through-bore 394. The central shaft 392 should extend through the base portion 374 or retract into the base portion 374, depending for example on the direction of rotation of the secondary drive shaft 366.

With continued reference to FIGS. 18-21, the tip assembly 306 preferably further includes an implant engagement gear 410. In preferred embodiments, the implant engagement gear 410 is configured to engage teeth 74 of the gear member 16 of the implant 10 (see, e.g., FIG. 2) such that when the implant engagement gear 410 is rotated, the gear member 16 of the implant 10 is rotated about the longitudinal axis 18 and the inner member 12 translates along the longitudinal axis to either expand or contract the implant 10. A series of gears (e.g., gears 412, 414, and 416) transfer rotation of the primary drive shaft 354 to the implant engagement gear 410. For example, rotation of implant engagement gear 410 causes rotation of distal gear 356. The distal gear 356 may engage a first primary central gear 412 disposed on the pin 376 such that rotation of the distal gear 356 causes rotation of the first primary central gear 412 about the pin axis 377. The first primary central gear 412 may be a bevel gear, for example. The distal gear 356 and the first primary central gear 412 may have rotational axes that are perpendicular, for example, the tool axis 308 and the pin axis 377. A second primary central gear 414 may be fixedly engaged to the first primary central gear 412 such that rotation of the central gear 412 causes rotation of the second primary central gear 414. The second primary central gear 414 may engage secondary transfer gear 416 such that rotation of the second primary central gear 414 causes rotation of the primary transfer gear 416. The gears 414, 416 may each be spur gears, for example. Pin 418 may secure primary transfer gear 416 to upper plate 372. The primary transfer gear 416 may rotate about the pin 418. The primary transfer gear 416 may engage the implant engagement gear 410 such that rotation of the primary transfer gear 416 causes rotation of the implant engagement gear 410. Accordingly, when the primary drive shaft 354 is rotated, the implant engagement gear 410 rotates causing the implant 10 to either expand or contract.

In an exemplary use of the angling inserter tool 300 with the implant 10, the angling inserter tool 300 initially engages the slots 52 of the implant 10 via the arms 400 and implant engagement gear 410 engages gear member 16 via their respective teeth. The secondary drive shaft 366 may then be driven (e.g., rotated) causing the second gear mechanism (e.g., distal gear 368, central gear 402, proximal gear portion 398) to advance the central shaft 392. For example, rotation of the secondary drive shaft 366 rotates the distal gear 368 about the tool axis 308 which rotates the secondary central gear 402 about the pin axis 376 which rotates the proximal gear portion 398 about the tool axis 308 to cause the central shaft 392 to advance toward opening 54. The threaded tip portion 396 enters into the opening 54 engaging the threads in opening 54 as well as engaging the through-hole 84 of locking member 80. As discussed previously, the locking member 80 should be engaged such that the gear member 16 may rotate freely. The implant 10 may then be placed in a desired location, for example, in the vertebral space. If desired, the tip assembly 306 can be angled relative to the tool axis 308, allowing the implant to be placed around or behind certain anatomical structures. As previously described, the knob 332 on the tool 300 may be rotated to cause the tip assembly 306 to angulate. For example, rotation of the knob 332 may cause longitudinal movement of the blocks 336 to cause translation of the internal shaft 320, thus moving the tip assembly 306 and causing rotation of the tip assembly 306 about the pin 376. The primary drive shaft 354 may then be driven (e.g., rotated) causing the primary gear mechanism (e.g., gears 356, 410, 412, 414, 416), for example, to rotate the gear member 16 on the implant 10. For example, rotation of the primary drive shaft 354 rotates the distal gear 356 about the tool axis 308 which rotates the first primary central gear 412 about the pin axis 377 which rotates the second primary central gear 414 about the pin axis 377. Rotation of the second primary central gear 414 rotates the primary transfer gear 416 about an axis generally parallel to the pin axis 377 which rotates the implant engagement gear 410 about an axis generally parallel to pin axis 377. The implant engagement gear 410 engages the gear member 16 on the implant causing the gear member 16 to rotate about longitudinal axis 18. As discussed above, the rotation of the gear member 16 results in the movement of the inner member 12 causing the implant 10 to either expand or contract, depending on the direction the gear member 16 is rotated. Once the desired height for the implant 10 is reached, the angling inserter tool 300 may be disengaged from the implant 10. It should be understood that the angling inserter tool 300 can be disengaged from the implant 10 even with the tip assembly 306 at any angle with respect to the tool axis 308. When the tool 300 is removed, the locking member 80 returns back to its initial state, thus preventing the gear member 16 from rotating as previously described.

While the preceding description of the angling inserter tool 300 is with respect to the implant 10, it should be understood that embodiments of the angling inserter tool 300 may be used for insertion and expansion of any of a variety of expandable implants for implantation into the spine, including vertebral body spacers for vertebral body replacement and expandable cages for insertion into the disc space.

Referring to FIGS. 24-27, an expandable trial assembly 420 is shown that may be used in the implanting of an expandable implant, such as implant 10 (FIG. 2), in accordance with embodiments of the present invention. In preferred embodiments, the trial assembly 420 may be used to distract adjacent vertebral bodies and to give a measurement of the distraction. In this manner, the trial assembly 420 may give a measurement of the desired height for the subsequent expansion of the implant 10, for example. As illustrated, the expandable trial assembly 420 may comprise a handle portion 422, a cylindrical base portion 424, and an expandable tip assembly 426. In the illustrated embodiment, the handle portion 422 extends downward from the cylindrical base portion 424. As illustrated, the expandable tip assembly 426 may be disposed at the distal end 432 of the cylindrical base portion 424. The expandable trial assembly 420 has a tool axis 430 that extends through the trial assembly 420 from the proximal end 433 to the distal end 432 of the cylindrical base portion 424.

Figures 24, 25:
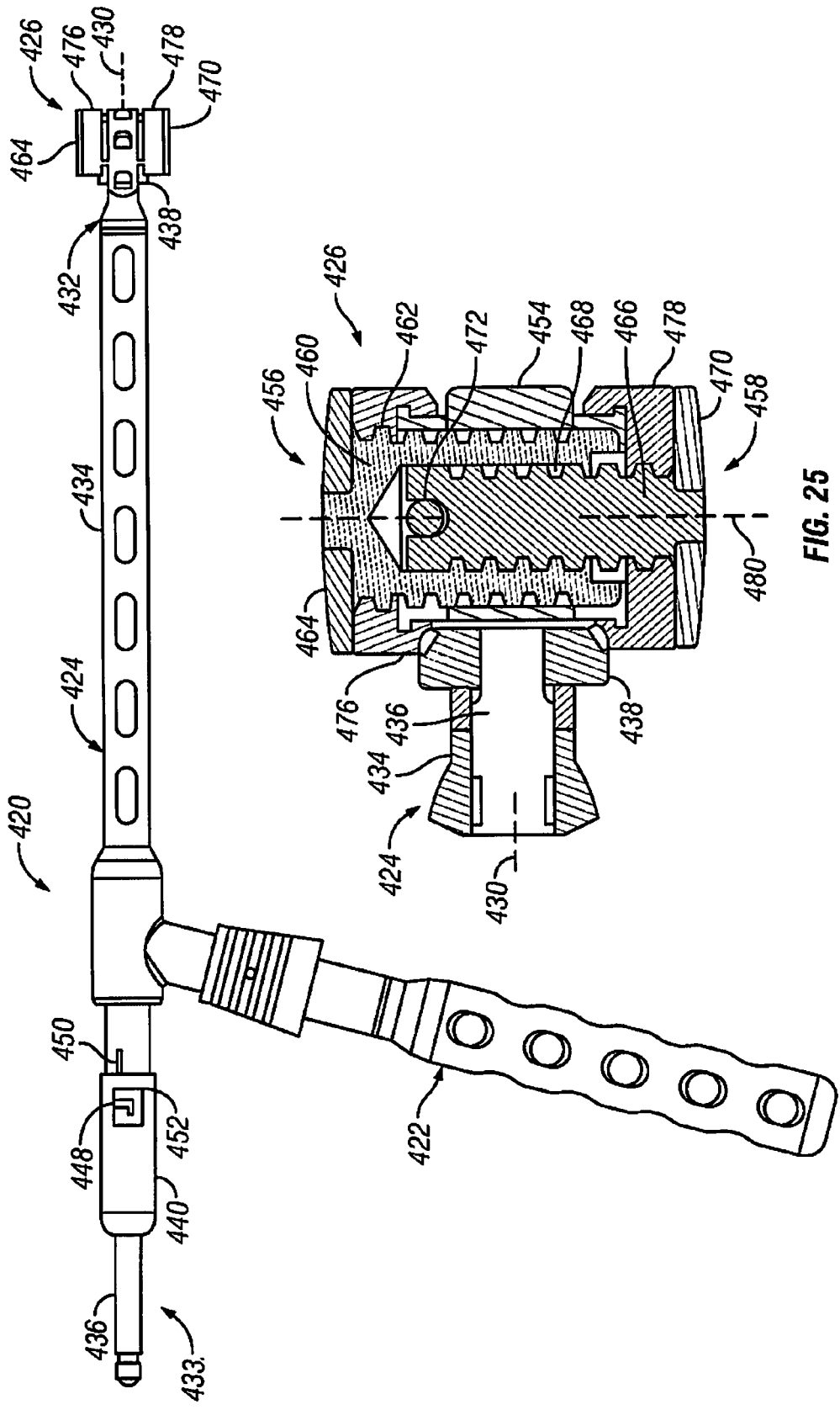
FIG. 24 is a view of an expandable trial assembly of one embodiment of the present invention in a contracted position.
FIG. 25 is a cross-sectional view of the expandable tip assembly of the expandable trial assembly of FIG. 24 in a contracted position.

In preferred embodiments, the cylindrical base portion 424 may include an outer cylinder 434 and a drive shaft 436. The drive shaft 436 may be coaxial with the outer cylinder 434 wherein the drive shaft 436 is inside the outer cylinder 434. In preferred embodiments, the drive shaft 436 is a generally cylindrical body. In present embodiments, the drive shaft 436 can rotate about the tool axis 433. A distal gear 438 is located on the drive shaft 436 at the distal end 432, as best seen in FIGS. 25 and 27. Rotation of the drive shaft 436 rotates the distal gear 438. The teeth of the distal gear 438 are not illustrated for simplicity.

Figure 28:
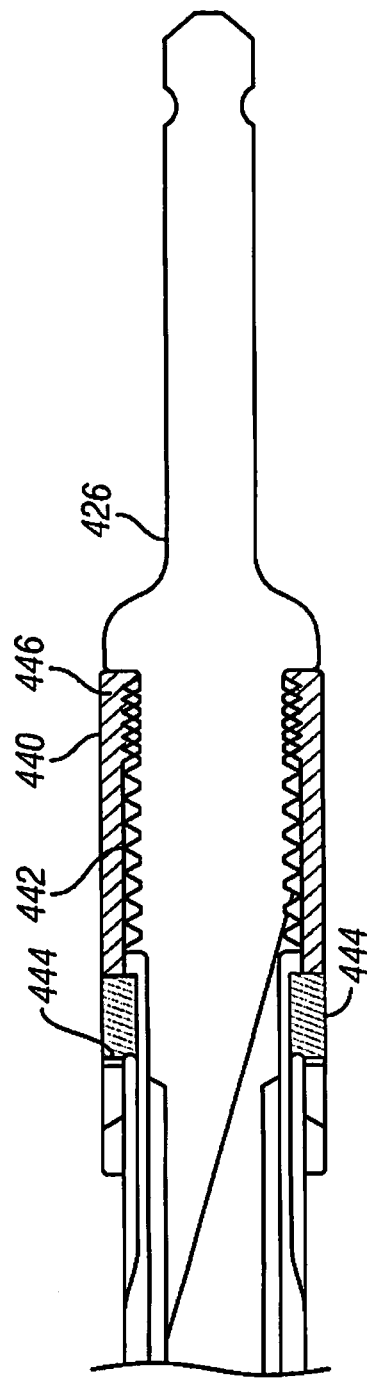
FIG. 28 is a cross-sectional view of one embodiment of the proximal end of the expandable trial assembly of FIG. 25 showing the scale portion.
Figure 29:
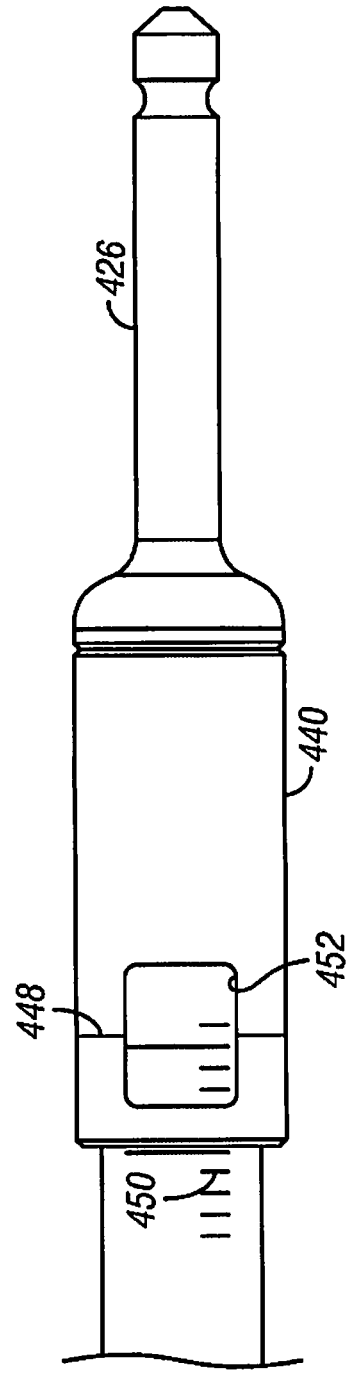
FIG. 29 is a view of one embodiment of the proximal end of the trial assembly of FIG. 25 showing the scale portion.

Referring to FIGS. 24, 26, and 28-29, the cylindrical base portion 424 further includes scale 440 at proximal end 433. The scale 440 may be in the general form of a cylindrical section. As best seen in FIGS. 28 and 29, at least a portion of the scale 440 may be internally threaded with threads. The scale 440 may be keyed to the outer cylinder 434. For example, locking mechanism 444 may secure the scale 440 to the outer cylinder 434, as best seen in FIG. 28. As seen in FIGS. 26 and 29, at least a portion of the drive shaft 436 may be threaded, for example, in the general region of the scale 440. The threaded portion 446 of the drive shaft 436 may engage the threads of the scale 440. Accordingly, rotation of the drive shaft 426 should cause the scale 440 to move longitudinally. Visual indicators 448, 450 may be placed on the scale and/or the outer cylinder 434 to show, for example, the amount of expansion of the expandable tip assembly 426. The visual indicators 448, 450 may be in the form of numbers, lines, combinations thereof or the like etched or otherwise formed on the scale 440 and/or the outer cylinder 434. In preferred embodiments, the scale 440 also includes a viewing window 452.

Referring to FIGS. 24-27, the expandable tip assembly 426 will now be described in more detail in accordance with embodiments of the present invention. As illustrated, the expandable tip assembly 426 may include a housing 454 which may be in the form of a rounded end. The expandable tip assembly 426 further may include an outer member 456 and an inner member 458 which may be telescopingly received within the inner member 458 and the outer member 456. The outer member 456 may generally comprise a generally cylindrical body 460 having external threads 462 on at least a portion thereof. An endplate 464 may be coupled to the outer member 456. The inner member 458 may comprise a generally cylindrical body 466 having external threads 468 on at least a portion thereof. An endplate 470 may be coupled to the inner member 458. While trial endplates 464, 470 are shown on the tip assembly 426, it should be appreciated that endplates having a different footprint may be used in accordance with embodiments of the present invention. For example, the endplates 464, 470 may be articulating (e.g., ball and socket type joint) to allow for measurement of sagittal alignment/angulation in addition to height. A One or more pins 472 may be used to secure the inner and outer members 456, 458 from rotational movement. The pins 472 may be disposed in corresponding slots 474 (best seen in FIG. 26) of the inner and outer members 456, 458.

In preferred embodiments, the expandable tip assembly 426 may further include upper gear member 476 and lower gear member 478. While not illustrated, the upper and lower gear members 476, 478 may each include outer gear teeth on at least a portion of their exterior surfaces that engage the distal gear 438 of the cylindrical base portion 424. Accordingly, rotation of the distal gear 438 about the tool axis should cause the upper and lower gear members 476, 478 to each rotate about the tip axis 480, as best seen in FIGS. 25 and 27. The upper gear member 476 is engaged with the external threads 462 of the outer gear member 458 and the lower gear member 478 is engaged with the external threads 468 of the inner member 458. Accordingly, because the outer and inner members 456, 458 are locked in rotational position by the one or more pins 472, rotation of the upper and lower gear members 476, 478 should cause the tip assembly 426 to either expand or contract. For example, rotation in one direction should cause the endplates 464, 470 to expand (or translate vertically outward) while rotation in the opposite direction should cause the endplates 464, 470 to contract (or translate vertically inward).

In an exemplary use of the expandable trial assembly 420, the trial assembly 420 may be inserted into a desired position in a patient's spine, for example, in a vertebral space, in a contracted position, as shown in FIGS. 24 and 25. The drive shaft 436 may then be rotated which causes expansion of the expandable tip assembly 426. FIGS. 26 and 27 illustrate the tip assembly 426 in an expanded position. For example, rotation of the drive shaft 436 rotates the distal gear 438 about the tool axis 430 which in turn rotates upper gear member 476 and lower gear member 478 about the tip axis 480. Rotation of the upper gear member 476 and the lower gear member 478 results in movement of the outer member 456 and the inner member 458 causing the expandable tip assembly 426 to either expand or contract, depending on the direction the drive shaft 436 is rotated. Once the desired expansion for the tip assembly 426 is reached, the expansion can be measured using the scale 440 at proximal end 433. The tip assembly 426 can then be contracted by rotation of the drive shaft 436 and then removed from the patient's body. An expandable implant, such as implant 10, can then be positioned in the patient's body in a manner that will be evident to one of ordinary skill in the art with the benefit of this disclosure. Once positioned in the body, the expandable implant can then be expanded to a desired expansion based on the measured expansion of the expandable trial assembly 420.

While the invention herein disclosed has been described by means of specific embodiments and applications thereof, numerous modifications and variations can be made thereto by those skilled in the art without departing from the scope of the invention as set forth in the claims.

What is claimed is:

1. A system for inserting an implant comprising:
a trial assembly configured for insertion between vertebrae in a patient and removal therefrom, wherein the trial assembly comprises:
a handle portion;
a cylindrical base portion coupled to the handle portion, wherein the cylindrical base portion comprises:
an outer cylinder;
a drive shaft configured to be coaxially received in the outer cylinder, wherein the drive shaft includes a gear at its distal end, wherein the drive shaft is configured to rotate about a longitudinal axis of the cylindrical base portion; and
a scale configured to threadingly receive the drive shaft within the scale; and
a tip assembly configured to expand, wherein the tip assembly comprises:
an outer member;
an upper gear member configured to engage the gear on the drive shaft and engage the outer member;
an inner member configured to be coaxially received within the outer member; and
a lower gear member configured to engage the gear on the drive shaft and engage the inner member,
wherein the scale is configured to measure expansion of the tip assembly and
wherein the upper gear member and the lower gear member are capable of moving with respect to each other;
an expandable implant configured for insertion into a patient's spine, the expandable implant having a longitudinal axis and comprising a gear member configured to expand the expandable implant; and
the expandable implant configured to be inserted between the vertebrae in the patient and expanded, wherein the scale on the trial assembly provides a measurement of expansion of the tip assembly to give a measurement for a height of expansion of the expandable implant; and
an inserter tool comprising: an inserter tip assembly having a base portion and a central shaft disposed in a throughbore in the base portion, wherein the central shaft is configured to engage the expandable implant, arms for engaging slots of the expandable implant and an implant engagement gear for engaging the gear member of the expandable implant, a primary gear mechanism configured to transfer rotation of a primary drive shaft to the expandable implant to cause expansion of the expandable implant; and a secondary gear mechanism configured to transfer rotation of a secondary drive shaft to the central shaft, wherein the inserter tool is configured to cause the tip assembly of the inserter tool to angulate.

2. The system of claim 1, wherein the scale is keyed to the outer cylinder.

3. The system of claim 1, wherein the outer cylinder comprises one or more visual indicators of the expansion of the trial assembly, and wherein the scale includes a viewing window for the one or more visual indicators.

4. The system of claim 3, wherein the scale comprises one or more visual indicators of the expansion of the trial assembly.

5. The system of claim 1, wherein an endplate for engaging a first vertebral body is coupled to the inner member, and wherein an endplate for engaging a second vertebral body is coupled to the outer member.

6. The system of claim 1, wherein a pin secures the inner and outer members in rotational position with respect to one another.

7. The system of claim 1, wherein the expandable implant comprises:

an inner member having a hollow interior portion and a threaded external portion and including a first end portion configured to engage the first vertebral body; and an outer member having a hollow interior portion configured to coaxially receive the inner member therein and including a second end portion configured to engage a second vertebral body, wherein the inner and outer members are moveable relative to each other along the longitudinal axis of the expandable implant;

the gear member positioned coaxial to the inner member and the outer member and axially fixed to the outer member and freely rotatable with respect to the outer member, wherein the gear member threadingly engages the threaded portion of the inner member.

8. The system of claim 1, wherein the inserter tool has a longitudinal axis and is configured for insertion of the expandable implant between the vertebrae, wherein the inserter tool comprises:

a handle portion;

a cylindrical base portion coupled to the handle portion, wherein the cylindrical base portion comprises:

an outer cylinder;

an internal shaft configured to be coaxially received within the outer cylinder;

the primary drive shaft configured to be coaxially received within the internal shaft; and the secondary drive shaft configured to be coaxially received within the primary drive shaft; and the inserter tip assembly positioned at a distal end of the base portion, wherein the internal shaft is configured to engage the inserter tip assembly such that the inserter tip assembly is configured to rotate about a pin coupled between the base portion and the inserter tip assembly upon distal advancement of the internal shaft.

* * * * *